(12) United States Patent
Jensen et al.

(10) Patent No.: US 11,565,230 B2
(45) Date of Patent: Jan. 31, 2023

(54) SYSTEMS AND METHODS FOR SYNTHESIZING CHEMICAL PRODUCTS, INCLUDING ACTIVE PHARMACEUTICAL INGREDIENTS

(71) Applicant: Massachusetts Institute of Technology, Cambridge, MA (US)

(72) Inventors: Klavs F. Jensen, Lexington, MA (US); Timothy F. Jamison, Cambridge, MA (US); Allan S. Myerson, Cambridge, MA (US); Jean-Christophe M. Monbaliu, Esneux (BE); Mohsen Behnam, Worcester, MA (US); Shin Yee Wong, Singapore (SG); Nopphon Weeranoppanant, Suphanburi (TH); Eve Marie Revalor, Rognes (FR); Torsten Stelzer, Old San Juan, PR (US); Jie Chen, Evanston, IL (US); Andrea Adamo, Cambridge, MA (US); David R. Snead, Atlanta, GA (US); Ping Zhang, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 99 days.

(21) Appl. No.: 16/988,827

(22) Filed: Aug. 10, 2020

(65) Prior Publication Data

US 2020/0368710 A1 Nov. 26, 2020

Related U.S. Application Data

(62) Division of application No. 15/504,049, filed as application No. PCT/US2015/045220 on Aug. 14, 2015, now Pat. No. 10,780,410.

(Continued)

(51) Int. Cl.
*B01J 19/00* (2006.01)
*B01J 19/18* (2006.01)
(Continued)

(52) U.S. Cl.
CPC ......... *B01J 19/004* (2013.01); *B01J 19/0093* (2013.01); *B01J 19/18* (2013.01);
(Continued)

(58) Field of Classification Search
None
See application file for complete search history.

(56) References Cited

U.S. PATENT DOCUMENTS 2,421,714 A  6/1947  Rieveschl
2,441,498 A  5/1948  Lofgren et al.
(Continued)

FOREIGN PATENT DOCUMENTS

EP  2374534 A1  10/2011
EP  2427166 B1  10/2013
(Continued)

OTHER PUBLICATIONS

BR112017002624-4, Oct. 27, 2020, Brazilian Office Action.
(Continued)

*Primary Examiner* — Jennifer A Leung
(74) *Attorney, Agent, or Firm* — Wolf, Greenfield & Sacks, P.C.

(57) ABSTRACT

Systems and methods for synthesizing chemical products, including active pharmaceutical ingredients, are provided. Certain of the systems and methods described herein are capable of manufacturing multiple chemical products without the need to fluidically connect or disconnect unit operations when switching from one making chemical product to making another chemical product.

21 Claims, 8 Drawing Sheets

Related U.S. Application Data

(60) Provisional application No. 62/038,039, filed on Aug. 15, 2014.

(51) Int. Cl.
*A61K 31/14* (2006.01)
*A61K 31/167* (2006.01)

(52) U.S. Cl.
CPC ............ *A61K 31/14* (2013.01); *A61K 31/167* (2013.01); *B01J 2219/0002* (2013.01); *B01J 2219/0004* (2013.01); *B01J 2219/00011* (2013.01); *B01J 2219/0081* (2013.01); *B01J 2219/00795* (2013.01); *B01J 2219/00799* (2013.01); *B01J 2219/00806* (2013.01); *B01J 2219/00813* (2013.01); *B01J 2219/00817* (2013.01); *B01J 2219/00822* (2013.01); *B01J 2219/00831* (2013.01); *B01J 2219/00833* (2013.01); *B01J 2219/00835* (2013.01); *B01J 2219/00871* (2013.01); *B01J 2219/00873* (2013.01); *B01J 2219/00889* (2013.01); *B01J 2219/00907* (2013.01); *B01J 2219/00909* (2013.01); *B01J 2219/00918* (2013.01); *B01J 2219/00986* (2013.01)

(56) References Cited

U.S. PATENT DOCUMENTS

| | | | |
|---|---|---|---|
| 5,164,159 | A | 11/1992 | Hayashi et al. |
| 5,259,812 | A | 11/1993 | Kleinsek |
| 5,275,741 | A | 1/1994 | Miano et al. |
| 5,925,732 | A | 7/1999 | Ecker et al. |
| 6,376,729 | B1 | 4/2002 | Merrill et al. |
| 6,495,103 | B2 | 12/2002 | Hettinger |
| 6,638,482 | B1 | 10/2003 | Ackley et al. |
| 6,688,325 | B2 | 2/2004 | Hettinger |
| 6,737,026 | B1 | 5/2004 | Bergh et al. |
| 6,782,307 | B2 | 8/2004 | Wilmott et al. |
| 6,806,087 | B2 | 10/2004 | Kibby et al. |
| 7,172,735 | B1 | 2/2007 | Lowe et al. |
| 7,241,423 | B2 | 7/2007 | Golbig et al. |
| 7,790,124 | B2 | 9/2010 | Matteo |
| 7,854,902 | B2 | 12/2010 | Matteo |
| 8,075,778 | B2 | 12/2011 | Guenther et al. |
| 8,426,630 | B2 | 4/2013 | McQuade et al. |
| 8,540,939 | B2 | 9/2013 | Niesz et al. |
| 8,584,349 | B2 | 11/2013 | Scannon et al. |
| 8,594,848 | B2 * | 11/2013 | Ludwig .............. G01N 35/0092 422/62 |
| 8,709,231 | B2 | 4/2014 | Lascoste et al. |
| 8,821,718 | B2 | 9/2014 | Blomberg et al. |
| 10,780,410 | B2 | 9/2020 | Jensen et al. |
| 11,185,839 | B2 | 11/2021 | Adamo et al. |
| 2002/0012616 | A1 | 1/2002 | Zhou et al. |
| 2002/0028504 | A1 | 3/2002 | MacCaskill et al. |
| 2003/0017467 | A1 | 1/2003 | Hooper et al. |
| 2003/0188740 | A1 | 11/2003 | Tribelsky et al. |
| 2004/0063992 | A1 | 4/2004 | Chiang et al. |
| 2005/0042149 | A1 | 2/2005 | Bard |
| 2005/0079109 | A1 | 4/2005 | Meier |
| 2005/0175519 | A1 | 8/2005 | Rogers, Jr. et al. |
| 2005/0177280 | A1 | 8/2005 | Almstetter et al. |
| 2006/0163069 | A1 | 7/2006 | Prak et al. |
| 2007/0144967 | A1 | 6/2007 | Guenther et al. |
| 2008/0233018 | A1 | 9/2008 | Van Dam et al. |
| 2008/0233653 | A1 | 9/2008 | Hess et al. |
| 2008/0288089 | A1 | 11/2008 | Pettus et al. |
| 2009/0043141 | A1 | 2/2009 | Mazanec et al. |
| 2009/0282978 | A1 | 11/2009 | Jensen et al. |
| 2010/0278706 | A1 | 11/2010 | Mueh et al. |
| 2010/0285575 | A1 | 11/2010 | Michiels |
| 2010/0324157 | A1 | 12/2010 | Bauman et al. |
| 2011/0104043 | A1 | 5/2011 | Niesz et al. |
| 2011/0132822 | A1 | 6/2011 | Kaw |
| 2011/0240924 | A1 | 10/2011 | Repasky |
| 2011/0258837 | A1 | 10/2011 | Scannon et al. |
| 2011/0306539 | A1 * | 12/2011 | Shen ...................... A61P 33/00 514/202 |
| 2012/0061869 | A1 | 3/2012 | Boeckx et al. |
| 2012/0076692 | A1 | 3/2012 | Miraghaie |
| 2012/0094366 | A1 | 4/2012 | Ludwig |
| 2012/0107175 | A1 | 5/2012 | Satyamurthy et al. |
| 2012/0296448 | A1 | 11/2012 | Balentine et al. |
| 2012/0325469 | A1 | 12/2012 | Olson et al. |
| 2013/0026100 | A1 | 1/2013 | Gebauer |
| 2013/0260419 | A1 | 10/2013 | Ransohoff et al. |

FOREIGN PATENT DOCUMENTS

| | | |
|---|---|---|
| JP | H06-167500 A | 6/1994 |
| JP | H08-131819 A | 5/1996 |
| JP | H10-501167 A | 2/1998 |
| JP | 2002-186851 A | 7/2002 |
| JP | 2002-193848 A | 7/2002 |
| JP | 2003-531875 A | 10/2003 |
| JP | 2004-508919 A | 3/2004 |
| JP | 2006-239638 A | 9/2006 |
| JP | 2006-527073 A | 11/2006 |
| JP | 2007-515646 A | 6/2007 |
| JP | 2010-535703 A | 11/2010 |
| JP | 2011-509907 A | 3/2011 |
| JP | 2011-218349 A | 11/2011 |
| JP | 2013-524212 A | 6/2013 |
| KR | 10-2011-0111253 A | 10/2011 |
| WO | WO 95/26796 A1 | 10/1995 |
| WO | WO 01/89681 A2 | 11/2001 |
| WO | WO 2005/063372 A2 | 7/2005 |
| WO | WO 2008/109877 A1 | 9/2008 |
| WO | WO 2010/132412 A2 | 11/2010 |
| WO | WO 2012/078677 A2 | 6/2012 |
| WO | 2013/025775 A1 | 2/2013 |
| WO | WO 2013/123254 A1 | 8/2013 |
| WO | WO 2017/192595 A1 | 11/2017 |

OTHER PUBLICATIONS 2017-508044, Oct. 2, 2020, Japanese Notice of Allowance.
Australian Office Action dated Jan. 14, 2021 for Application No. AU 2019268159.
Canadian Office Action dated Jul. 14, 2021 for Application No. CA 2957410.
Mexican Office Action dated Oct. 4, 2021 for Application No. MX/A/2017/002033.
Japanese Notice of Allowance dated Oct. 2, 2020 for Application No. 2017-508044.
Brazilian Office Action dated Oct. 27, 2020 for Application No. BR112017002624-4.
Japanese Office Action dated Apr. 30, 2021 for Application No. JP 2020-024181.
Mexican Office Action dated May 11, 2021 for Application No. MX/A/2017/002033.
JP 2020-024181, Apr. 30, 2021, Japanese Office Action.
MX/A/2017/002033, May 11, 2021, Mexican Office Action.
Australian Office Action dated Nov. 26, 2021 for Application No. AU 2019268159.
Korean Office Action dated Oct. 29, 2021 for Application No. KR 10-2017-7006712.
Examination Report No. 1 dated Nov. 23, 2018 for Application No. AU 2015301544.
Extended European Search Report dated Mar. 5, 2018 for Application No. EP 15832380.8.
European Office Action dated Apr. 24, 2020 for Application No. 15832380.8.
Japanese Office Action dated Aug. 15, 2019 for Application No. 2017-508044.
International Search Report and Written Opinion for PCT/US2015/045220 dated Nov. 24, 2015.

(56) References Cited

OTHER PUBLICATIONS

International Preliminary Report on Patentability dated Mar. 2, 2017 for Application No. PCT/US2015/045220.
[No Author Listed], Corning Advanced-Flow Reactors—Low-Flow Reactor Pamphlet. 2016. 3 pages.
[No Author Listed], Critical Temperature and Pressure, dated Jul. 18, 2013. Purdue University. Retrieved from internet archive for https://www.chem.purdue.edu/gchelp/liquids/critical.html. (Year: 2013).
[No Author Listed], Defense Advanced Research Project Agency (DARPA), Broad Agency Announcement, Pharmacy on Demand (PoD), Defense Sciences Office (DSO), DARPA-BAA-11-05. Oct. 21, 2010;1-41.
[No Author Listed], WHO Model List of Essential Medicines, 18th List, Apr. 2013, 47 pages, http://www.who.int/medicines/publications/essentialmedicines/en/index.html (accessed Aug. 3, 2013).
Abboud et al., Factory shift: new prescription for drug makers: update the plants; after years of neglect, industry focuses on manufacturing; FDA acts as a catalyst; the three-story blender. Wall Street J. Sep. 3, 2003, 5 pages.
Ahmed-Omer et al., Preparation of fluoxetine by multiple flow processing steps. Org Biomol Chem. May 21, 2011;9(10):3854-62. doi:10.1039/c0ob00906g. Epub Mar. 30, 2011.
Anderson, Using continuous processes to increase production. Org Process Res Dev. 2012;16(5):852-69.
Benyahia et al., A plant-wide dynamic model of a continuous pharmaceutical process. Ind Eng Chem Res. Oct. 2012; 51(47):15393-412.
Bogdan et al., The continuous-flow synthesis of ibuprofen. Angew Chem Int Ed Engl. 2009;48(45):8547-50. doi: 10.1002/anie.200903055.
Hartman et al., Deciding whether to go with the flow: evaluating the merits of flow reactors for synthesis. Angew Chem Int Ed Engl. Aug. 8, 2011;50(33):7502-19. doi: 10.1002/anie.201004637. Epub Jun. 27, 2011.
Hartman et al., Microchemical systems for continuous-flow synthesis. Lab Chip. Sep. 7, 2009;9(17):2495-507. doi: 10.1039/b906343a. Epub May 28, 2009.
Hessel, Novel process windows—gate to maximizing process intensification via flow chemistry. Chem Eng Technol. Nov. 2009;32(11):1655-81.
Hogan, A little goes a long way. Nature. Jul. 27, 2006;442:351-2. Erratum in: Nature. Jul. 27, 2006;442:351-2.
Jimenez-Gonzalez et al., Key green engineering research areas for sustainable manufacturing: a perspective from pharmaceutical and fine chemicals manufacturers. Org Process Res Dev. Jul. 2011; 15(4):900-11.
Malet-Sanz, Continuous flow synthesis. A pharma perspective. J Med Chem. May 10, 2012;55(9):4062-98. doi: 10.1021/jm2006029. Epub Feb. 27, 2012.
Mason et al., Greener approaches to organic synthesis using microreactor technology. Chem Rev. Jun. 2007;107(6):2300-18. Epub Mar. 21, 2007.
Plumb, Continuous processing in the pharmaceutical industry—changing the mindset. Chem Eng Res Des. Trans IChemE, Part A. Jun. 2005;83(A6):730-8.
Poechlauer et al., Continuous processing in the manufacture of active pharmaceutical ingredients and finished dosage forms: an industry perspective. Org Process Res Dev, 2012;16(10):1586-90.
Proctor et al., Continuous processing in the pharmaceutical industry, in Green Chemistry in the Pharmaceutical Industry, Ch. 11, 221-42. Wiley-VCH: Weinheim, Germany. 2010.
Reilly, The preparation of lidocaine. J Chem Educ. Nov. 1999;76(11):1557.
Roberge et al., Microreactor technology and continuous processes in the fine chemical and pharmaceutical industry: is the revolution underway? Org Process Res Dev. 2008;12(5):905-10.
Roberge et al., Microreactor technology: a revolution for the fine chemical and pharmaceutical industries? Chem Eng Technol. 2005;28(3):318-23.
Schaber et al., Economic analysis of integrated continuous and batch pharmaceutical manufacturing: a case study. Ind Eng Chem Res. Jul. 2011;50(17):10083-92.
Snead et al., End-to-end continuous flow synthesis and purification of diphenhydramine hydrochloride featuring atom economy, in-line separation, and flow of molten ammonium salts. Chem Sci. 2013;4(7):2822-27. doi: 10.1039/c3sc50859e.
Stankiewicz et al., Process intensification: transforming chemical engineering. Chem Eng Prog. Jan. 2000;96:22-34.
Sugasawa et al., A new simple synthesis of 1,4-benzodiazepines. J Heterocyclic Chem. Apr. 1979; 16(3):445-8.
Thomas, The reality of continuous processing. Manuf Chem. Apr. 1, 2005, accessed Jun. 21, 2017 at http://www.manufacturingchemist.com/technical/article_page/The_reality_of_continuous . . . , 5 pages.
Webb et al., Continuous flow multi-step organic synthesis. Chem Sci. 2010, 1, 675-80. doi: 10/1039/c0sc00381f.
Wegner et al., Ten key issues in modern flow chemistry. Chem Commun (Camb). Apr. 28, 2011;47(16):4583-92. doi: 10.1039/c0cc05060a. Epub Mar. 15, 2011.
Whitesides, The origins and the future of microfluidics. Nature. Jul. 27, 2006;442(7101):368-73.
Wiles et al., Micro Reaction Technology in Organic Synthesis. 453 pages (submitted in 2 parts), CRC Press: Boca Raton, 2011.
Yamauchi et al., A facile and efficient preparative method of methyl 2-arylpropanoates by treatment of propiophenones and their derivatives with iodine or iodine chlorides. J Org Chem. 1988;53(20):4858-9.
U.S. Appl. No. 16/098,333, filed Nov. 1, 2018, Adamo et al.
PCT/US2015/045220, Nov. 24, 2015, International Search Report and Written Opinion.
PCT/US2015/045220, Mar. 2, 2017, International Preliminary Report on Patentability.
EP 15832380.8, Mar. 5, 2018, Extended European Search Report.
AU 2015301544, Nov. 23, 2018, Examination Report.
JP 2017-508044, Aug. 15, 2019, Japanese Office Action.
EP 15832380.8, Apr. 24, 2020, European Office Action.
AU 2019268159, Nov. 26, 2021, Office Action.
KR 10-2017-7006712, Oct. 29, 2021, Office Action.
MX/A/2017/002033, Oct. 4, 2021, Office Action.
AU 2019268159, Jan. 14, 2021, Australian Office Action.
CA 2967410, Jul. 14, 2021, Canadian Office Action.
Japanese Notice of Allowance dated Feb. 22, 2022 for Application No. 2020-024181.
Canadian Office Action dated Apr. 4, 2022, for Application No. 2957410.
Karpinski et al., Precipitation Processes. In: Handbook of Industrial Crystallization. 2002. Myerson, Ed. Chapter 6: 141-160.
Korean Office Action dated Jun. 14, 2022, for Application No. KR 10-2022-7010220.
KR 10-2022-7010220, Jun. 14, 2022, Korean Office Action.
Japanese Office Action dated Oct. 7, 2022, for Application No. JP2021-151829.

\* cited by examiner

SYSTEMS AND METHODS FOR SYNTHESIZING CHEMICAL PRODUCTS, INCLUDING ACTIVE PHARMACEUTICAL INGREDIENTS

RELATED APPLICATIONS

This application is a division of U.S. patent application Ser. No. 15/504,049, filed Feb. 15, 2017, which is a National Stage Application under 35 U.S.C. § 371 of International Patent Application No. PCT/US2015/045220, filed on Aug. 14, 2015, which claims priority under 35 U.S.C. § 119(e) to U.S. Provisional Application Ser. No. 62/038,039, filed Aug. 15, 2014, each of which is incorporated herein by reference in its entirety for all purposes.

GOVERNMENT SPONSORSHIP

This invention was made with government support under Contract No. N66001-11-C-4147 awarded by the Space and Naval Warfare Systems Center. The government has certain rights in the invention.

TECHNICAL FIELD

Systems and methods for synthesizing chemical products, including active pharmaceutical ingredients are generally described.

BACKGROUND

Recently, pharmaceutical and biotechnology industries have experienced periods of slowed growth and increased costs associated with the development of new chemical products and active pharmaceutical ingredients. While individual processes involved in certain pharmaceutical manufacturing are transitioning to continuous-like processes, pharmaceutical facilities generally still rely on batch or semi-batch techniques to produce complex chemical products. Current processes are typically tailored to manufacture a single specific active pharmaceutical ingredient and generally require large, expensive, and static setups. While continuous processes are suggested to offer numerous benefits, including reduced cost, complete infrastructure and systems capable of complex continuous manufacturing of chemical products and active pharmaceutical ingredients do not exist. The ability to synthesize and formulate chemical products (and, in some cases, multiple chemical products) in a single continuous, self-contained, system remains elusive.

SUMMARY

Systems and methods for synthesizing chemical products, including active pharmaceutical ingredients, are provided. Certain of the systems and methods described herein are capable of manufacturing multiple chemical products without the need to fluidically connect or disconnect unit operations when switching from one making chemical product to making another chemical product. The subject matter of the present invention involves, in some cases, interrelated products, alternative solutions to particular problem, and/or a plurality of different uses of one or more systems and/or articles.

In one aspect, a system for producing a chemical product is provided. The system can comprise, in some embodiments, a first module comprising a first unit operation, a second unit operation fluidically connected to the first unit operation in parallel, and a first bypass conduit fluidically connected to the first unit operation and the second unit operation in parallel, and a second module fluidically connected to the first module in series, the second module comprising a third unit operation, a fourth unit operation fluidically connected to the third unit operation in parallel, and a second bypass conduit fluidically connected to the third unit operation and the fourth unit operation in parallel.

In another aspect, a method for producing chemical products is provided. The method can comprise, in some embodiments, transporting a first fluid comprising a first chemical reactant through a first module comprising a chemical reactor and at least a second unit operation fluidically connected in parallel, and through a second module connected to the first module in series, the second module comprising at least one separator and at least a fourth unit operation fluidically connected in parallel, such that the first chemical reactant within the first fluid is reacted to form a first chemical product that is transported out of the second module, and subsequently, transporting a second fluid comprising a second chemical reactant through the first module and the second module such that the second chemical reactant within the second fluid is reacted to form a second chemical product, without forming the first chemical product, such that the second chemical product is transported out of the second module, wherein no additional unit operations are newly fluidically connected to the first and second modules between the steps of transporting the first fluid and transporting the second fluid, and no unit operations are fluidically disconnected from the first and second modules between the steps of transporting the first fluid and transporting the second fluid.

In another aspect, a method for the continuous production of an ingestible pharmaceutical composition within a reactor system is provided. The method can comprise, in some embodiments, transporting an input fluid comprising a chemical reactant through a reactor such that the chemical reactant is reacted, within the reactor, to produce an active pharmaceutical ingredient within a reactor output stream, transporting the reactor output stream to a separator and separating at least a portion of the active pharmaceutical ingredient from at least a portion of another component of the reactor output stream to produce a separator product stream having a higher concentration of the active pharmaceutical ingredient than the reactor output stream, and transporting the separator product stream from the separator to a formulator in which the active pharmaceutical ingredient is converted into the ingestible pharmaceutical composition, wherein the amount of the active pharmaceutical ingredient within the ingestible pharmaceutical composition that is output from the formulator is output at a rate of at least about 20 grams/day, and wherein the reactor system, including the reactor, the separator, and the formulator, are contained within a housing occupying a volume of less than about 100 $ft^3$ and/or occupying a footprint of less than about 10 $ft^2$.

Other advantages and novel features of the present invention will become apparent from the following detailed description of various non-limiting embodiments of the invention when considered in conjunction with the accompanying figures. In cases where the present specification and a document Incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
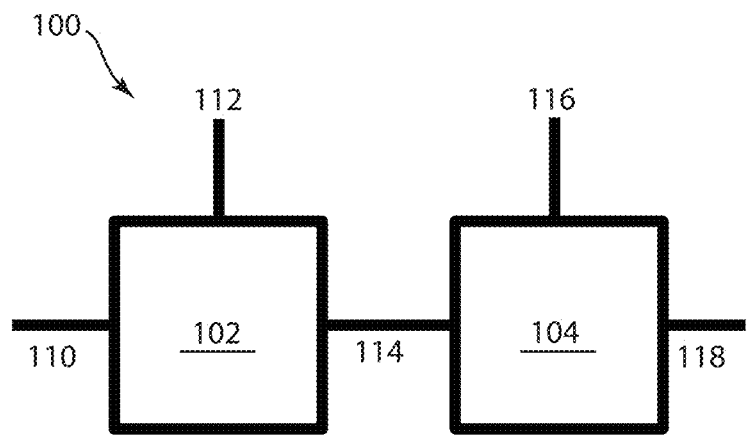
FIG. 1 is a schematic illustration of a system for producing a chemical product, according to one set of embodiments.

Systems and methods related to synthesizing chemical products, including active pharmaceutical ingredients, are generally described.

The ability to manufacture chemical products (e.g., active pharmaceutical ingredients (APIs)) in a portable, self-contained, and/or readily reconfigurable chemical process remains generally elusive. For example, chemical synthesis, purification, formulation, and final packaging steps typically require large-scale facilities and expensive operations. These facilities generally require long timescales to develop manufacturing methods and to proceed from synthesizing of chemical products and ingredients to the release of a finished chemical (e.g., pharmaceutical) product. Furthermore, manufacturing delays and shortages can often result when large batches of chemical products fail quality control testing. Additionally, the facilities used to manufacture chemical products are typically designed for the manufacturing of one particular chemical product, and generally require extensive disassembly and reassembly in order to manufacture additional chemical products.

Certain of the systems and methods described herein can provide one or more advantages over traditional chemical (e.g., pharmaceutical) manufacturing systems and methods.

Some embodiments described herein may be used in a variety of applications that can benefit from the ability to synthesize chemical products in a continuous process. For example, a large percentage of active pharmaceutical ingredients are typically formulated in discrete batch or semi-batch processes. The ability to synthesize active pharmaceutical ingredients in a continuous manner can allow for a significant reduction in footprints of required facilities, as well as the development of novel synthesis methods. In addition, the use of continuous flow synthesis in a compact, reconfigurable manufacturing system can allow for high-throughput, on-demand production of chemical products (e.g., active pharmaceutical ingredients).

Certain of the embodiments described herein provide tools and related techniques for the synthesis of chemical products (e.g., active pharmaceutical ingredients) in a portable, self-contained system. For example, in one set of embodiments, multiple-step chemical processing can be achieved using a series of modules comprising unit operations used for chemical synthesis, purification, formulation, and/or final packaging of one or more chemical products. In some cases, synthesis of two or more chemical products can be achieved without connecting or disconnecting modules and/or unit operations between the time a first chemical product is synthesized and the time a second chemical product is synthesized. That is to say, in some embodiments, a first chemical product can be synthesized within the system over a first period of time, and a second chemical product can be synthesized within the system at a second period of time that does not overlap with the first period of time, without the need for fluidically connecting or disconnecting modules or unit operations between the first and second periods of time.

In addition, chemical products (e.g., active pharmaceutical ingredients) may be synthesized, in some cases, at a high throughput in a system that occupies a relatively small footprint. In some embodiments, the process is automated, allowing a user to start an operation and track the synthesis of chemical products throughout the system. The systems and methods described herein may be coupled with electronic controls and/or other automation systems to allow for operation without the need for process interruptions or shut downs. The systems and methods described herein, in some embodiments, are portable. In some such embodiments, the portable systems require only an external electrical power supply for effective operation.

The use of certain of the inventive synthesis systems and methods described herein offers one or more advantages over typical large-scale batch systems. Non-limiting examples of such advantages include the ability for one user/operator to operate the system, performing multiple unit operations (e.g., one or more reactions, one or more separations, etc.) at the same time at different locations within the same uninterrupted system. Generally, batch systems would require each unit operation to be physically and temporally disconnected, requiring much longer times, footprints, and workforce requirements, as compared to certain of the synthesis systems described herein. Additionally, certain of the unit operations described herein can allow for simplification of chemical synthesis steps (e.g., selecting chemicals to obtain shorter chemical processing sequences, selecting appropriate additives and/or solvents to yield simplified purification steps, and/or forming chemical products without the need to remove impurities).

In one set of embodiments, systems and methods related to producing one or more chemical products are described. FIG. 1 includes a schematic illustration of system 100 according to one set of embodiments, which can be used to produce one or more chemical products. In some embodiments, the system comprises one or more modules. The module can contain at least one unit operation. The unit operation can be used to perform a step of a chemical process. In some embodiments, the system comprises a plurality of modules connected in series. For example, in certain embodiments, the system comprises a first module and a second module fluidically connected to the first module in series. Referring to FIG. 1, for example, system 100 comprises module 102 and module 104, fluidically connected in series via conduit 114. In some such embodiments, each of the modules within the series can be used to perform a single step of a multi-step chemical process. For example, referring to FIG. 1, module 102 can be used to perform the first step in a multi-step chemical synthesis process, and module 104 can be used to perform the second step of a multi-step chemical synthesis process. While two modules are illustrated in FIG. 1, additional modules could also be used. In some embodiments, the system comprises at least three, at least four, at least five, at least ten, or more modules.

Module 102 may be, according to certain embodiments, configured to receive a fluid (which may, in some embodiments, comprise a chemical reactant, a chemical product, and/or a solvent, as described below) via conduit 110. In some embodiments, module 102 may be configured to receive an optional additional fluid (which may, in some embodiments, contain a second chemical reactant, a second solvent, etc.) via conduit 112. In some such embodiments, module 102 comprises a unit operation configured to perform a process that produces one or more output streams having a substantially different chemical composition than input stream(s) 110 and 112, as described in more detail below. As one example, in some embodiments, module 102 contains a reactor in which the chemical reactant received via conduit 110 is reacted to form a chemical reaction product. The output stream produced by module 102 can be transported out of module 102 via conduit 114. In some embodiments, module 104 may be configured to receive the output stream produced by module 102 via conduit 114. In some embodiments, module 104 is configured to receive an additional fluid via conduit 116. In some cases, module 104 can contain a unit operation that can be configured to perform a process that produces one or more output streams having a substantially different chemical composition than input stream(s) 114 and 116. For example, in some embodiments, module 104 contains a reactor in which a chemical reactant received via conduit 114 is reacted to form a chemical reaction product. As another example, module 104 could comprise a separator in which a chemical product received via conduit 114 is at least partially separated from another component. The output stream produced by module 104 can be transported out of module 104 via conduit 118.

In some embodiments, the system for producing a chemical product comprises a first module and a second module fluidically connected in series. By connecting multiple modules in series, one can perform a series of chemical processing steps as part of an overall chemical synthesis process. In some such embodiments, the first module can be used to perform a first step of the chemical synthesis process, and the second module can be used to perform a second step of the chemical synthesis process.

Figure 2A:
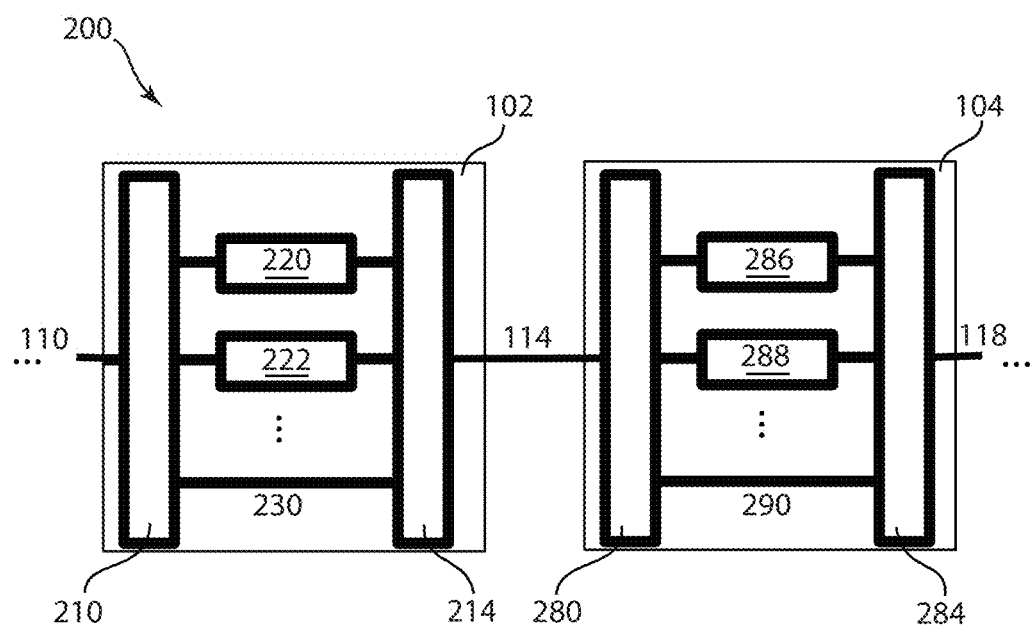
FIG. 2A is, according to certain embodiments, a schematic illustration of a system for producing a chemical product.

An exemplary system comprising multiple modules is illustrated schematically in FIG. 2A. In the exemplary embodiment of FIG. 2A, system 200 comprises first module 102 fluidically connected in series by conduit 114 to second module 104. First module 102 comprises first unit operation 220, second unit operation 222 fluidically connected to the first unit operation in parallel, and bypass conduit 230 fluidically connected to the first unit operation and the second unit operation in parallel. Second module 104 comprises a third unit operation 286, a fourth unit operation 288 fluidically connected to the third unit operation in parallel, and bypass conduit 290 fluidically connected to the third unit operation and the fourth unit operation in parallel.

In some embodiments, unit operations and/or bypass conduits are fluidically connected by one or more manifolds. For example, in the exemplary embodiment of FIG. 2A, first unit operation 220, second unit operation 222, and bypass conduit 230 are fluidically connected by manifold 210 and manifold 214. In addition, in FIG. 2A, third unit operation 286, fourth unit operation 288, and bypass conduit 290 are fluidically connected via manifold 280 and manifold 284.

In some embodiments, additional modules can also be included within the system. In certain embodiments, additional unit operations and/or bypass conduits can also be fluidically connected to each other within each module. In some embodiments, two or more modules in the system (e.g., the first module and the second module) comprise identical arrangements of unit operations.

As introduced above, a module can comprise two or more unit operations fluidically connected in parallel. For example, in some cases, the module comprises a first unit operation and a second unit operation fluidically connected to the first unit operation in parallel. As described herein, a unit operation generally refers to a device configured to perform a function that produces one or more output streams having a substantially different chemical composition than at least one of the streams input to the unit operation. Generally, an output stream has a substantially different chemical composition than an input stream when the relative abundance of at least one fluid component within the output stream is at least 5 wt % different (or, in some cases, at least 10 wt % different or at least 25 wt % different) than the relative abundance of that component in the input stream. The wt % difference of a particular fluid component can be determined by calculating the absolute value of the difference between the wt % of the fluid component within the output stream and the wt % of the fluid component within the input stream, and dividing the calculated absolute value by the wt % of the fluid component within the input stream. In other words, the wt % difference of a particular fluid component may be calculated as:

$$\Delta w = \frac{|w_o - w_i|}{w_i}$$

where $\Delta w$ is the wt % difference of the particular component, $w_o$ is the wt % of the fluid component within the output stream, and $w_i$ is the wt % of the fluid component within the input stream.

In some embodiments, more than two unit operations may be fluidically connected in parallel within a module. For example, in some cases, at least three, at least four, at least five, at least ten, or more unit operations can be fluidically connected in parallel within a module. A number of unit operations may be suitable for use in certain of the modules described herein. Non-limiting examples of unit operations include reactors and non-reactor unit operations (e.g., separators, mixers, etc.), as described in more detail below.

In some cases, the module may comprise at least one bypass conduit fluidically connected to one or more unit operations in parallel. For example, in some embodiments, the module comprises a bypass conduit, a first unit operation, and a second unit operation, wherein each of the bypass conduit, the first unit operation, and the second unit operation are fluidically connected to each other in parallel. The bypass conduit can include any suitable type of conduit (e.g., a tube, a pipe, a channel, and the like). The bypass conduit generally produces one or more output streams having a substantially similar chemical composition as the stream input to the bypass conduit. In some embodiments, the bypass conduit can be used to bypass a unit operation within a module in cases where a unit operation does not need to be performed by the module. For example, if the chemical synthesis process being performed includes only four steps, and eight modules are provided, fluid may be transported through the bypass conduits of four of the modules that are not needed to perform the chemical process.

Figure 2B:
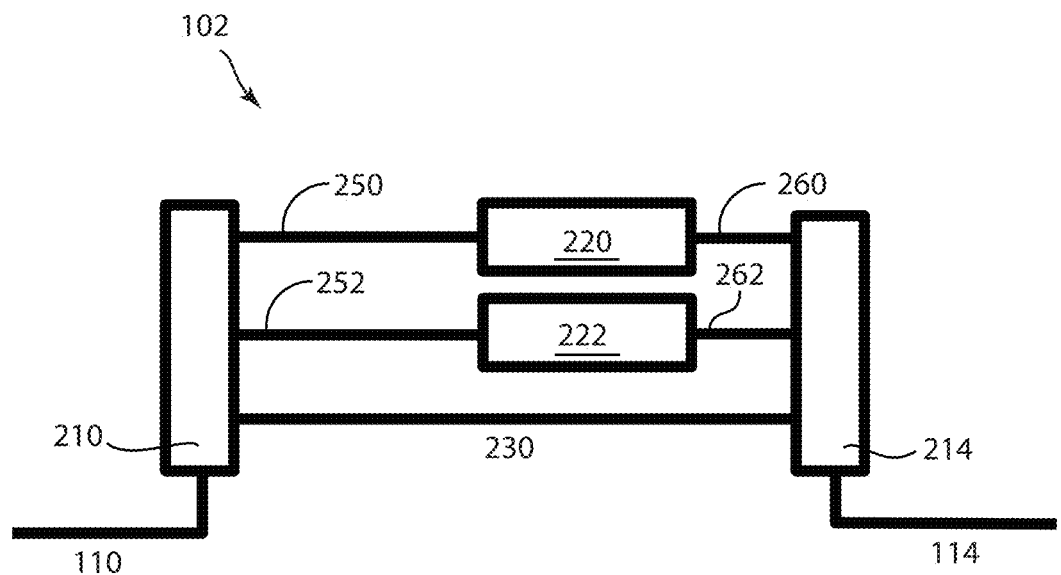
FIG. 2B-E are, according to some embodiments, schematic illustrations of modules for producing a chemical product.
Figure 2C:
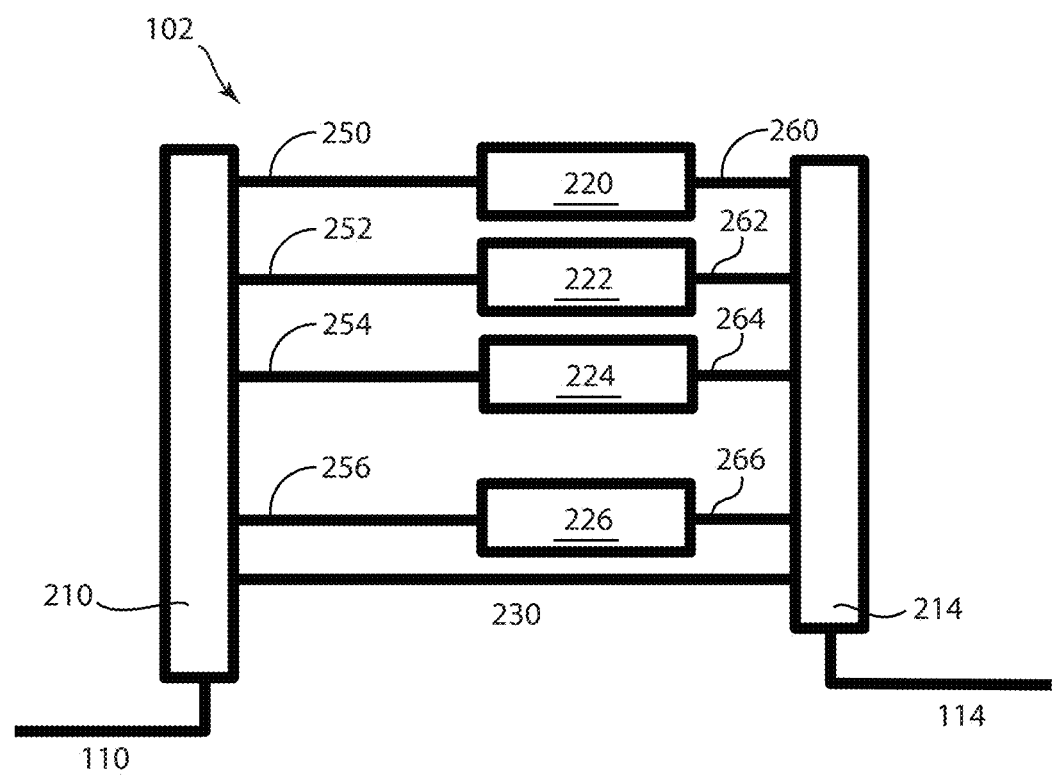

In some embodiments, a module comprises two unit operations and a bypass conduit. As illustrated in the exemplary embodiment of FIG. 2B, module 102 comprises two unit operations fluidically connected in parallel. For example, exemplary module 102 comprises first unit operation 220 and second unit operation 222 fluidically connected to first unit operation 220 in parallel. In some embodiments, the module may optionally include more than two unit operations, as illustrated in FIG. 2C and described in more detail below. Referring to FIG. 2B, unit operations 220 and 222 are fluidically connected via conduits 250 and 252, respectively, to inlet manifold 210 and conduits 260 and 262, respectively, to outlet manifold 214. Module 102 comprises bypass conduit 230 fluidically connected in parallel to first unit operation 220 and second unit operation 222.

FIG. 2C is an exemplary schematic illustration of a module in which more than two unit operations are fluidically connected in parallel. In the exemplary embodiment of FIG. 2C, module 102 comprises optional third unit operation 224 and optional fourth unit operation 226, each connected to first unit operation 220 and second unit operation 222 in parallel. Module 102 in the exemplary embodiment of FIG. 2C also comprises bypass conduit 230 fluidically connected in parallel to first unit operation 220 and second unit operation 222 (and, as illustrated in FIG. 2B, fluidically connected in parallel to third unit operation 224 and fourth unit operation 226). Unit operations 224 and 226 are fluidically connected via conduits 254 and 256, respectively, to inlet manifold 210 and conduits 264 and 266, respectively, to outlet manifold 214.

Manifolds, as described herein, may comprises a series of pre-connected conduits, channels, valves, or the like for selecting one or unit operations in which a fluid and/or fluids may be transported. One of ordinary skill in the art will understand that a valve generally refers to a device which directs and/or controls the flow of a fluid (e.g., by opening or closing a conduit) without fluidically connecting and/or disconnecting a conduit. Non-limiting examples of valves include mechanical valves, ball valves, check valves, butterfly valves, piston valves, pneumatic valves, electronic valves, and hydraulic valves. In some embodiments, the valve comprises two or more ports (e.g., two port valves, three port valves, four port valves, etc.).

In certain embodiments, the manifold comprises a plurality of outlets, with each of the plurality of outlets fluidically connected to a single unit operation or a single bypass conduit within the module. In some embodiments, the manifold(s) within the module can be configured such that fluid is selectively transported through a single unit operation within the module. In some embodiments, during operation, at least one of the modules (e.g., at least the first module) is operated such that at least about 95 wt %, at least about 99 wt %, at least about 99.9 wt %, or substantially all of an input fluid transported into the module is transported through only one of the first unit operation, the second unit operation, and the bypass (while less than about 5 wt %, less than about 1 wt %, less than about 0.1 wt %, or substantially none, respectively, of the input fluid is transported through the remaining fluidic pathways within the module). For example, an operator may, in some cases, select unit operation 220 by choosing an appropriate conduit and/or valve in manifold 210, transporting the fluid from the inlet to manifold 220 to unit operation 220. In some embodiments, the operator may select the appropriate conduit and/or valve in manifold 210 such that the fluid is transported through bypass conduit 230.

In some cases, a module may comprise an optional second manifold to add an additional optional fluid (e.g., comprising one or more reagents and/or solvents, as described below) to a selected unit operation. For example, referring to FIG. 2D, inlet manifold 210 is fluidically connected to conduit 110 which may, in some cases, transport a fluid (e.g., a first chemical reactant) to one or more unit operations fluidically connected in parallel. Module 102 may comprise conduit 112 to transport a second fluid (e.g., a second chemical reactant) to one or more unit operations fluidically connected in parallel via inlet manifold 212. Inlet manifold 210 and/or inlet manifold 212 may be configured such that one of the unit operations can be selectively activated to perform a step of a chemical process. Alternatively, inlet manifold 210 and/or inlet manifold 212 may be configured such that fluid may be transported through the bypass conduit. For example, in some cases, a user may select conduit 250 such that a first fluid is transported to unit operation 220 and/or may select conduit 240 such that a second fluid is also transported to unit operation 220. In some embodiments, a fluid transported from inlet manifold 210 is mixed (e.g., with a mixer) with a fluid transported from inlet manifold 212 before transporting the fluid to a unit operation.

In some embodiments, transporting the fluid comprises pumping (e.g., via a pump) the fluid through a conduit, a unit operation, and/or a bypass conduit. It may be advantageous, in some cases, to transport fluid without the use of a pump. For example, in may be advantageous, in some embodiments (e.g., where the fluid contains suspended solids), to transport fluid via gravity. One advantage of transporting the fluid via gravity is the prevention of the agglomeration of solids, which could block fluid flow within a conduit or unit operation.

As described herein, in some embodiments, at least one of the unit operations within the module(s) is a reactor. For example, referring to FIG. 2B, in some embodiments, unit operation 220 and/or unit operation 222 is a reactor. Referring back to FIG. 2C, in some embodiments, unit operation 224 and/or unit operation 226 is a reactor. Referring back to FIG. 2B, in some embodiments, reactor 220 is configured to receive an input stream via conduit 250 comprising a chemical reactant and to output a chemical product (e.g., a chemical product, an intermediate chemical product, or an API) to an exit stream via conduit 260. In certain embodiments, referring now to FIG. 2D, reactor 220 is configured to receive a first input stream via conduit 250 and a second input stream via conduit 240, and to output a chemical product to an exit stream via conduit 260.

In general, a reactor comprises a vessel (e.g., a tank, a tube, a coil, a pipe, or the like) configured to perform a chemical reaction. A reactor may be configured, in some cases, to take in a chemical reactant (e.g., from a conduit fluidically connected to a reservoir containing the chemical reactant, from a conduit fluidically connected to another reactor, and/or from a conduit fluidically connected to a non-reactor unit operation) and to produce an intermediate of a target chemical product or to produce the target chemical product itself.

Any suitable type of reactor may be used including, but not limited to, a plug flow reactor, a packed bed reactor (e.g., a catalytic packed bed reactor), a continuously stirred tank reactor, or any other suitable reactor type. For example, in certain embodiments, the reactor comprises a stainless steel tube, which can be coiled to reduce its size. In some embodiments, the reactor is packed with various materials such as glass or metal beads, sieves and/or resins. In certain embodiments, the reactor comprises a polymer tube (e.g. comprising perfluoroalkoxy (PFA), ethylene tetrafluoroethylene (ETFE), polyether ether ketone (PEEK), or other polymer materials) of defined structures and dimensions (e.g. the internal diameter), which can be coiled and embedded in a rigid housing (e.g. stainless steel, aluminum, silicon carbide or other rigid materials) to ensure (a) heat conduction and (b) high resistance to mechanical stresses under various operating temperatures and pressures.

In some embodiments, the reactor has a relatively small volume. The use of reactors with relatively small volumes can, according to certain embodiments, aid in maintaining the portability of the overall synthesis process. In addition, it has been unexpectedly found that small reactors can be used while maintaining a relatively high reactant throughput. According to certain embodiments, one or more (or all) of the reactors within the system has a volume of less than or equal to about 1 liter, less than or equal to about 100 milliliters, less than or equal to about 10 milliliters, or less than or equal to about 5 milliliters. In some cases, one or more (or all) of the reactors within the system may be a microreactor (e.g., wherein the volume of the reactor is less than 1 milliliter). In some embodiments, one or more (or all) of the reactors within the system has a volume as little as 100 microliters, as little as 10 microliters, or less.

In some embodiments, the chemical reaction takes place in a continuous manner, as described below. In some embodiments, the chemical reaction may take place at a particular volumetric flow rate throughout the reactor. In certain embodiments, the flow rate is a variable flow rate. In some embodiments, the flow rate is a constant flow rate. In some embodiments, the chemical reaction takes place within a reactor at a flow rate ranging between about $1\times10^{-8}$ m$^3$/hr to about $1\times10^{-4}$ m$^3$/hr. In certain embodiments, the chemical reaction takes place within a reactor at a flow rate of at least about $1\times10^{-8}$ m$^3$/hr, at least about $1\times10^{-7}$ m$^3$/hr, at least about $1\times10^{-6}$ m$^3$/hr, or at least about $1\times10^{-5}$ m$^3$/hr. Other flow rates are also possible.

It may be advantageous, in some cases, for a reactor to be operated at an elevated pressure. Operating a reactor at elevated pressures offers several advantages as compared to operating a reactor at about atmospheric pressure. For example, in certain cases, operating reactors at elevated pressures can allow one to avoid boiling chemical reagents and/or solvents (which otherwise might be boiled at atmospheric pressure), which can allow one to perform chemical reactions which would not otherwise occur. In certain cases, operating the reactor at an elevated pressure can increase the reaction rate of the chemical reaction performed within the reactor. Another advantage to operating a reactor at elevated pressures includes removing offending reagents and byproducts that would otherwise clog the system and/or reduce the yield of the chemical product. For example, operating a reactor at elevated pressures may prevent the burning of a product (e.g., through overreaction). In some cases, for example, operating reactors at elevated pressures can prevent or reduce the formation of side products, which can remove the need for secondary purification steps between modules and/or unit operations. In some cases, operating a reactor at elevated pressures includes maintaining fluids in an aqueous phase (e.g., enabling a reduction of the volume required to operate the reactor), which may prevent the formation of solids that would otherwise clog the system.

In some embodiments, the one or more reactors within the system can be operated at a pressure of between about 15 psi and about 500 psi. In certain embodiments, the reactor is operated at a pressure greater than or equal to about 15 psi, greater than or equal to about 50 psi, greater than or equal to about 100 psi, greater than or equal to about 150 psi, greater than or equal to about 200 psi, greater than or equal to about 250 psi, greater than or equal to about 300 psi, or greater than or equal to about 400 psi. In some embodiments, the system comprises a back pressure regulator (e.g., to regulate the pressure within one or more unit operations) fluidically connected to one or more unit operations in parallel.

In certain embodiments, the reactor is operated at a relatively high temperature. Operating the unit operation at high temperatures (e.g., greater than about 40° C.) can, according to certain embodiments, offer a number of advantages. For example, operating a reactor at an elevated temperature can accelerate the rate of a chemical reaction performed in the reactor. In some cases, operating a unit operation at a high temperature may inhibit or substantially prevent the formation of solid in the reactor (e.g., by operating the unit operation at temperatures above the melting point of the solid). In some embodiments, the reactor is operated at a temperature ranging between about 20° C. and about 200° C. In certain embodiments, the reactor is operated at a temperature of greater than or equal to about 20° C., greater than or equal to about 40° C., greater than or equal to about 60° C., greater than or equal to about 90° C., greater than or equal to about 100° C., greater than or equal to about 120° C., greater than or equal to about 130° C., greater than or equal to about 150° C., or greater than or equal to about 180° C. Other temperature ranges may also be possible.

In certain embodiments, one or more of the unit operations described herein can be non-reactor unit operations. For example, referring back to FIG. 2A, unit operation 220 can, in some embodiments, be a non-reactor unit operation. Referring again to FIG. 2C, unit operation 224 can, in some embodiments, be a non-reactor unit operation. In certain embodiments, the non-reactor unit operation(s) is fluidically connected to one or more reactor unit operations in parallel. The non-reactor unit operation can be any type of unit operation that is not a reactor. For example, in some embodiments, the non-reactor unit operation is a separator. In certain embodiments, the non-reactor unit operation is a mixer.

In some embodiments, certain of the unit operations described herein can be separators. The separators can be used to at least partially separate an intermediate of a target chemical product and/or a target chemical product from at least one other component (i.e., the "removed component"). For example, in some embodiments, the separator can be used to at least partially separate a target chemical product or an intermediate of the target chemical product from a solvent, a reaction by-product, and/or an impurity. The separator can be configured to remove at least a portion of at least one removed component from an input stream, without chemically reacting the removed component(s), to produce a product stream that does not include the removed portion of the component. In some embodiments, the removed component can be retained within the separator, as might be observed, for example, in an absorptive separator. In some embodiments, the removed component can be transported out of the separator in a separate product stream. For example, in some cases, the separator may be configured such that a fluid stream comprising a target product entering the fluid separator will exit the separator in a first exit stream enriched in a target chemical product, and the removed component exits the separator in a second exit stream lean in the target chemical product. That is to say, the second exit stream may contain the target chemical product in an amount less than is contained in the feed stream. In some embodiments, the target chemical product comprises a desirable chemical product.

Figure 2D:
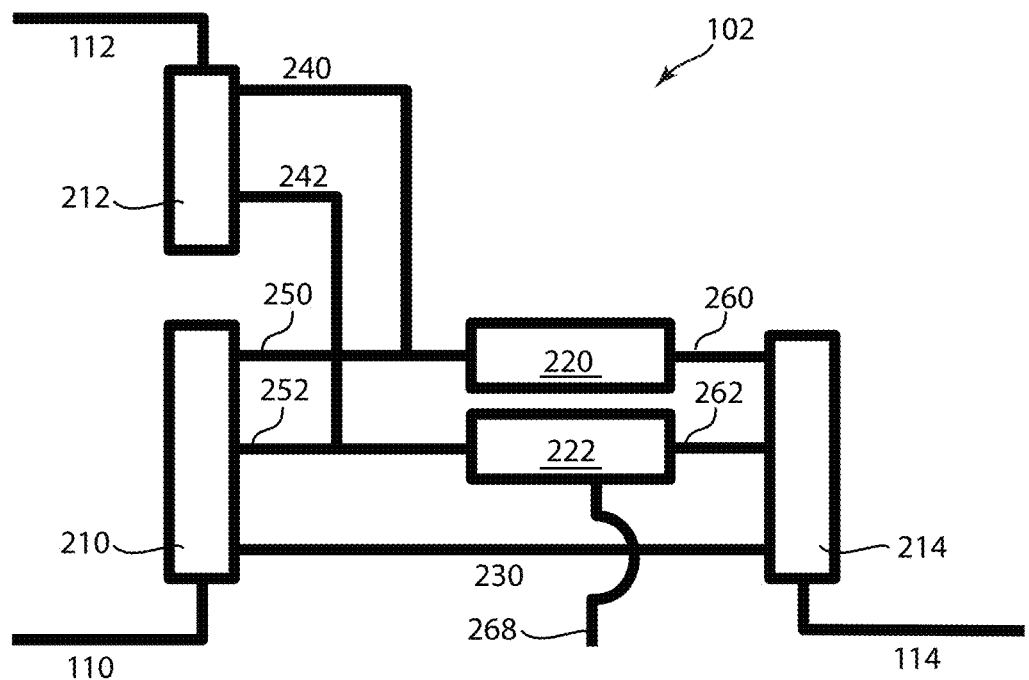

Referring to FIG. 2D, module 102 comprises separator 222. Separator 222 can be configured to receive an input stream via conduit 252, which can contain a chemical reaction product (e.g., a target chemical product or an intermediate of a target chemical product). The chemical reaction product can originate, for example, from a reactor upstream of separator 222. Separator 222 can be configured to at least partially separate the chemical reaction product from at least one other component of the input stream (e.g., a solvent). The separation process can result in the production of a first exit stream containing the chemical reaction product at a concentration greater than the concentration of the chemical reaction product in the input stream. The first exit stream can be transported via conduit 262 to manifold 214. The separation process can also result in the production of a second exit stream containing none of the chemical reaction product or containing the chemical reaction product at a concentration smaller than the concentration of the chemical reaction product in the input stream. The second exit stream can be transported via conduit 268, for example, to a waste collection unit configured to collect, for example, solvents, byproducts, etc. In some embodiments, transporting a fluid through the separator results in at least partially separating a chemical product from a chemical byproduct. For example, in some embodiments, the input stream transported via conduit 252 in FIG. 2D contains a chemical reaction product and a byproduct. In some such embodiments, separator 222 is operated such that the first exit stream transported via conduit 262 contains the chemical reaction product in a higher concentration than the concentration of the chemical reaction product in the input stream, and the second exit stream transported via conduit 268 contains the chemical reaction byproduct in a higher concentration than the concentration of the chemical reaction byproduct in the input stream. In some embodiments, transporting a fluid through the separator results in at least partially separating a chemical reaction product from a solvent. For example, in some embodiments, the input stream transported via conduit 252 in FIG. 2D contains a chemical reaction product and a solvent. In some such embodiments, separator 222 is operated such that the first exit stream transported via conduit 262 contains the chemical reaction product in a higher concentration than the concentration of the chemical reaction product in the input stream, and the second exit stream transported via conduit 268 contains the solvent in a higher concentration than the concentration of the solvent in the input stream.

In some embodiments, the weight ratio of the chemical product present in the first exit stream from the separator (e.g., the first exit stream transported via conduit 262 in FIG. 2D) and the chemical product present in the second exit stream from the separator (e.g., the second exit stream transported via conduit 268 in FIG. 2D) is at least about 2:1, at least about 3:1, at least about 5:1, at least about 10:1, at least about 50:1, at least about 100:1, or at least about 1000:1. In certain embodiments, the second exit stream from the separator (e.g., the second exit stream transported via conduit 268 in FIG. 2D) comprises substantially none of the target product.

Any of a variety of types of separators may be used in the systems and methods described herein. In some embodiments, the separator is a liquid-liquid separator. The liquid-liquid separator can be configured to take in a mixture of a first liquid and a second liquid, and produce a first product stream enriched in the first liquid relative to the mixture and a second product stream enriched in the second liquid relative to the mixture. In some embodiments, the liquid-liquid separator comprises a membrane (e.g., a membrane liquid-liquid separator). In some embodiments, the separator comprises chemically resistant polymeric materials (e.g., polyethylene, high density polyethylene (HDPE), PFA, ETFE, polytetrafluoroethylene (PTFE), ultra high molecular weight polyethylene (UHMWPE)), a rigid housing (e.g., stainless steel, aluminum) and the membrane. The membrane, in certain embodiments, may be semipermeable (i.e., the membrane permits the passage of one or more fluids but excludes the passage of a second fluid through the membrane). In the case of certain membrane-based separators, separation can be achieved by relying on the surface tension forces between the membrane, the first fluid in a mixture, and the second fluid in the mixture, as described, for example, in U.S. Patent Publication No. 2007/0144967 to Guenther et al. entitled "Fluid Separation" and U.S. Patent Publication No. 2009/0282978 to Jensen et al. entitled "Microfluidic Separators for Multiphase Fluid-Flow Based On Membranes", each of which is incorporated herein by reference in its entirety for all purposes. In some embodiments, the separator is a reverse osmosis separator. In certain embodiments, the liquid-liquid separator is a liquid-liquid gravity separator (e.g., a sedimentation liquid-liquid separator). In certain embodiments, the separator can comprise a settling tank and/or a continuous centrifuge. In some embodiments, the separator comprises a diaphragm. In certain embodiments, the diaphragm comprises a chemically resistant polymeric material (e.g., polyethylene, HDPE, PFA, ETFE, PTFE). In some cases, the separator may comprise a self-tuning pressure regulator.

In some embodiments, the separator is a retention column. The retention column can be configured to retain (e.g., by adsorbing, absorbing, or otherwise taking up) at least one component of a feed stream transported into the retention column. In some embodiments, the retention column is a drying column. In certain embodiments, the retention column comprises an adsorption medium. Non-limiting examples of an adsorption medium include carbon-based material (e.g., charcoal). In some embodiments, the carbon-based material comprises activated charcoal. Other adsorption media are also possible and those of ordinary skill in the art would be able to select a suitable adsorption medium based on the component desired to be removed from the feed stream.

It may be advantageous, in some embodiments, to operate the separator at elevated pressures (e.g., at any of the elevated pressures described elsewhere herein). For example, operating the separator at elevated pressures can, in certain embodiments, allow for separation to be followed immediately by a second high-pressure reaction (e.g., immediately transporting the separated liquid to a reactor fluidically connected to the separator) without the need to re-pressurize the liquid before it enter the second high-pressure reactor.

Figure 2E:
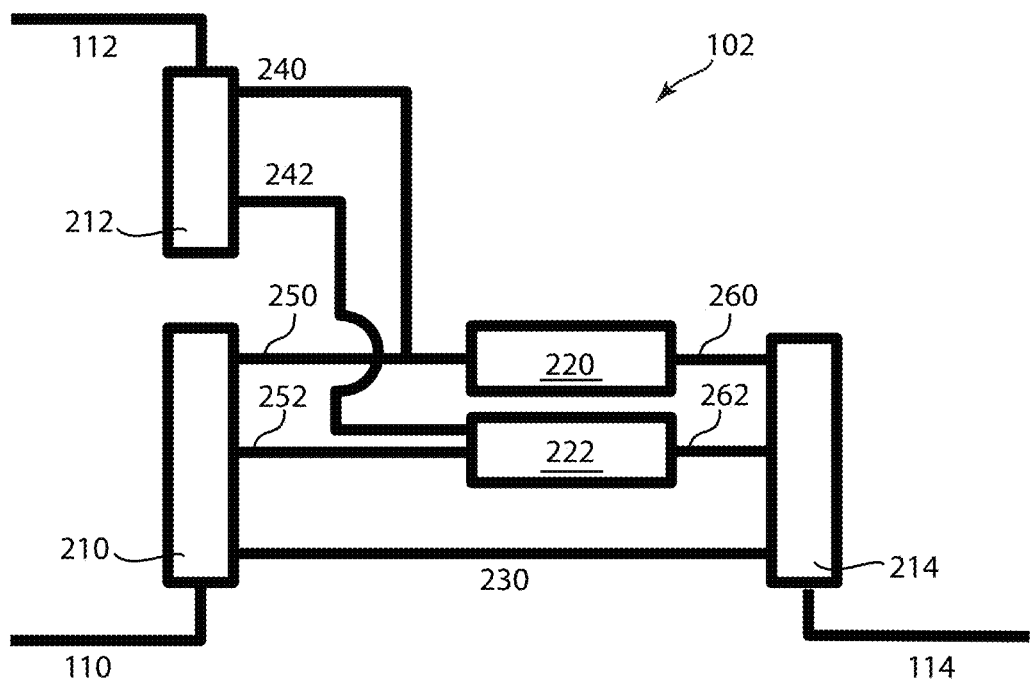

In some embodiments, a mixer is used as a non-reactor unit operation within a module. In certain embodiments, the mixer is fluidically connected to one or more unit operations (e.g., one or more reactors and/or one or more separators) in parallel. For example, referring to FIG. 2E, unit operation 222 may be a mixer. Mixer 222 may be configured, in some embodiments, to receive a first input stream via conduit 252 and a second input stream via conduit 242, and to output a mixed exit stream via conduit 262.

Any suitable type of mixer can be used. In some embodiments, the mixer comprises a junction between two or more fluidically connected conduits. In some embodiments, the mixer can be heated (e.g., using a heat exchanger, including any of the types of heat exchangers described below, or others). The fluid can be mixed using static mixers, in some embodiments. In some embodiments, the mixer comprises a stir bar, an impeller, or the like to facilitate mixing of the first input stream and the second input stream. For example, in certain embodiments, the mixer comprises a Y junction, a T junction, an arrow head, and/or a cross junction. In some embodiments, the mixer comprises a micromixer and/or an embedded static macromixer. The mixer may be constructed from any suitable material (e.g., PEEK, PTFE, ETFE, stainless-steel, glass or any other suitable materials). In certain embodiments, the mixer consists of a stainless-steel tube packed with glass microbeads (e.g., with an average diameter of at least about 100 μm).

In certain embodiments, the module comprises a heat exchanger. In some embodiments, the heat exchanger is fluidically connected (in parallel, or in series) to a unit operation (e.g., a reactor and/or one or more non-reactor unit operations). Generally, the heat exchanger is configured to add heat to and/or remove heat from a fluid within the reactor system. Any suitable type of heat exchanger can be employed. In some embodiments, the heat exchanger comprises a first fluid configured to exchange heat with a second fluid (e.g., by contacting a first conduit comprising the first fluid and a second conduit comprising the second fluid). For example, in certain embodiments, the heat exchanger is a double pipe heat exchanger. In some embodiments, the heat exchanger is a shell and tube heat exchanger. In certain embodiments, the heat exchanger is a plate heat exchanger. Other types of heat exchangers are also possible and will be generally known by those of ordinary skill in the art. In certain embodiments, the heat exchanger comprises a heater (e.g., an electric heater, a geothermal heater, a solar heater, a thermoelectric material (e.g., a Peltier device), and the like). In some embodiments, the heat exchanger comprises a cooling apparatus (e.g., a cooling liquid (e.g., a refrigerant or a solvent), a thermoelectric material (e.g., a Peltier device), and the like). In some embodiments, the heat exchanger is configured to transfer heat to and/or remove heat from a fluid within the reaction system without the use of a heat transfer fluid. For example, in some embodiments, the heat exchanger comprises a Peltier device, a resistive heating element, and the like.

As mentioned above, certain of the systems described herein can be used to produce chemical products. Some embodiments comprise transporting a fluid (e.g., a chemical reagent, a solvent, or combinations thereof) through the one or more modules fluidically connected in series. Some embodiments comprise transporting a first fluid (e.g., a chemical reagent, a solvent, or combinations thereof) through a first module and a second module fluidically connected to the first module in series to form a first chemical product (which is output from the second module).

In some such embodiments, the fluid is transported through a unit operation within the module to perform a step of a multi-step chemical synthesis. Some such embodiments comprise producing an exit stream from a module that is compositionally distinguishable from a fluid transported through an inlet stream of the module. For example, in some cases, a chemical product may be produced in an exit stream of a module by performing a reaction within a unit operation within the module. In some embodiments, the exit stream may be produced by mixing and/or reacting a first fluid and a second fluid in a unit operation. In some cases, the exit stream from the module may be produced by separating, in a unit operation of the module, a first component (e.g., the desired chemical product) from a second component (e.g., a solvent and/or a byproduct) in a fluid.

In certain embodiments, a module comprises a reactor and is configured to produce a chemical product (or an intermediate thereof) from a chemical reactant. In some such embodiments, the module is configured to receive a chemical reactant via an inlet, house a chemical reaction involving the chemical reactant, and to output a target chemical product (or an intermediate thereof) via an exit conduit. Referring to FIGS. 2A and 2B, for example, module 102 can be configured to receive an input stream containing a chemical reactant via conduit 110 and to output a stream containing a target chemical compound (or an intermediate thereof) via exit conduit 114.

Any suitable chemical reagent can be used in the systems and methods described herein. Generally, the type of reagent that is employed in the system will depend on the chemical product one wishes to produce. In some embodiments, the chemical reactant can be a precursor of an active pharmaceutical ingredient. For example, in some embodiments in which one wishes to produce diphenhydramine hydrochloride, dimethylaminoethanol may be used as a chemical reagent. One such process is described, for example, in Example 2 below. In certain embodiments in which one wishes to produce lidocaine, 2,6-xylidine may be used as a chemical reagent. One such process is described, for example, in Example 3 below. In some embodiments in which one wishes to produce diazepam, 5-chloro-2-methyl-aminobenzophenone may be used as a chemical reagent. On such process is described, for example, in Example 4 below. In some cases in which one wishes to produce fluoxetine, 3-chloropropiophenone may be used as a chemical reagent, as described in Example 5 below. Of course, other chemical reagents can also be used including, but not limited to, dimethylaminoethanol, chlorodiphenylmethane, chloroacetyl chloride, ammonia, methylamine, diethylamine, 3-chloropropiophenone, diisobutylaluminium hydride, 4-fluorobenzotrifluoride, and bromoacetyl chloride.

In some embodiments, a first fluid comprising a first chemical reactant is transported through a first module. The first module can comprise a chemical reactor and at least a second unit operation. The chemical reactor and the second unit operation can be fluidically connected in parallel. For example, in FIG. 2A, first unit operation 220 can comprise a reactor and can be fluidically connected to unit operation 222 (which can be a second reactor or a non-reactor unit operation (e.g., a separator, a mixer, etc.) in parallel. In some embodiments, the fluid comprising the chemical reactant is transported through the chemical reactor within the first module. In some such embodiments, the chemical reactant is reacted, within the reactor of the first module, to produce a chemical product (or an intermediate thereof). In some embodiments, the chemical product is an active pharmaceutical ingredient, as described in more detail below.

Any suitable type of reactor can be used in the first module, including any of the chemical reactors described elsewhere herein.

In some embodiments, two or more reactors can be fluidically connected within the first module. That is to say, in some embodiments, a first reactor is fluidically connected in parallel to a second reactor within the first module. For example, referring again to FIG. 2A, unit operation 220 and unit operation 222 may be, in some cases, the first reactor and the second reactor, respectively. In some such embodiments, the first reactor may be of a first type (e.g., having a first volume and/or configuration) and the second reactor may be of a second type that is different from the first type (e.g., having a second volume and/or configuration different from the first volume and/or configuration). Arranging multiple reactors in parallel within a single module can allow one to select a reactor type that is appropriate for a given chemical product production process.

In certain embodiments, the reactor within the first module is fluidically connected to a non-reactor unit operation in parallel. As described above, the non-reactor unit operation may be, in some cases a separator, a mixer, or any other suitable non-reactor unit operation. Referring to FIG. 2A, for example, in some embodiments unit operation 222 may be a separator. In some embodiments, unit operation 222 may be a mixer. In still other embodiments, unit operation 222 may be a second chemical reactor, and one or more additional unit operations (not shown in FIG. 2A), such as a mixer and/or a separator, may be fluidically connected to unit operations 220 and 222 in parallel.

Certain embodiments further comprise transporting at least a portion of the first fluid (e.g., at least a portion of the fluid output from the first module) through a second module fluidically connected to the first module in series. In some embodiments, the second module comprises a separator and at least one additional unit operation fluidically connected to the separator in parallel. For example, referring to FIG. 2A, unit operation 286 can be a separator, which can be fluidically connected to unit operation 288 in parallel. Unit operation 288 can be a reactor or a non-reactor unit operation (e.g., a mixer, an additional separator, etc.).

Any suitable type of separator can be used in the second module, including any of the separators described elsewhere herein.

In certain embodiments, at least a portion of the fluid transported out of the first module can be transported through the separator of the second module. For example, referring to FIG. 2A, the first fluid can be transported into module 102 via conduit 110. Within module 102, a reactant within the first fluid can be reacted (e.g., within unit operation 220, which can be a reactor) to produce a first chemical product (or a precursor of a chemical product). The chemical product can be transported out of module 102 via conduit 114. In some such embodiments, at least a portion of the fluid within conduit 114 can be transported to module 104. In some such embodiments, the fluid within conduit 114 can be transported through a separator within module 104 (e.g., unit operation 286, which can be a separator).

In some such embodiments, transporting the fluid through the separator of the second module results in at least partially removing a solvent. For example, referring to FIG. 2A, in some embodiments, conduit 114 comprises a chemical product and a solvent. In some such embodiments, unit operation 286 (which can be a separator) within second module 104 can be used to at least partially separate the chemical product from the solvent. In some such embodiments, at least a portion (or all) of the chemical product can be transported out of second module 104 via conduit 118.

In some embodiments, transporting the fluid (e.g., the first fluid and/or the second fluid) through the separator comprises at least partially removing an impurity. For example, referring to FIG. 2A, in some embodiments, conduit 114 comprises a chemical product and an impurity. In some such embodiments, unit operation 286 (which can be a separator) within second module 104 can be used to at least partially separate the chemical product from the impurity. In some such embodiments, at least a portion (or all) of the chemical product can be transported out of second module 104 via conduit 118.

In some embodiments, transporting the fluid through the separator of the second module comprises at least partially separating the fluid into a chemical product and a chemical byproduct. For example, referring to FIG. 2A, in some embodiments, conduit 114 comprises a chemical product and a chemical by-product (e.g., produced during the reaction performed in unit operation 220 of module 102). In some such embodiments, unit operation 286 (which can be a separator) within second module 104 can be used to at least partially separate the chemical product from the chemical by-product. In some such embodiments, at least a portion (or all) of the chemical product can be transported out of second module 104 via conduit 118.

In some embodiments, transporting the fluid (e.g., the first fluid and/or the second fluid) through the non-reactor unit operation comprises heating and/or cooling. In some embodiments, heating and/or cooling the fluid comprises transporting the fluid through a heat exchanger. In certain embodiments, the heat exchanger is fluidically connected to at least one additional unit operation in parallel.

Certain embodiments comprise heating the fluid in a heat exchanger fluidically connected to at least one additional unit operation in parallel. In some embodiments, transporting the fluid through a heat exchanger comprises cooling the fluid.

While two modules are illustrated in FIG. 2A, the system can include additional modules, for example, to perform additional steps of a multi-step chemical synthesis. For example, additional modules containing reactors may be included upstream or downstream of modules 102 and/or 104, to perform additional chemical reaction steps of the chemical synthesis process. As another example, additional modules containing additional separators can be included upstream or downstream of modules 102 and/or 104, to perform additional separation steps.

In some embodiments, the system is configured to produce two or more chemical products. As described above, some embodiments comprise transporting a first fluid (e.g., a chemical reagent, a solvent, or combinations thereof) through a first module and a second module fluidically connected to the first module in series to form a first chemical product. In some embodiments, after the first chemical product has been formed, a second fluid comprising a second chemical reactant can be transported through the first and second modules to form a second chemical product (which can be transported out of the second module).

In some cases, the system is configured to produce a first chemical product over a first period of time and then a second chemical product over a second period of time. In certain embodiments, the first period of time does not overlap the second period of time. In some embodiments, the first chemical product can be produced without producing the second chemical product during the first period of time. In some embodiments, the second chemical product can be produced without producing the first chemical product during the second period of time. For example, in some embodiments, the system can be operated such that the first chemical product is formed over a first period of time during which time the second chemical product is not formed, and the second chemical product is formed over a second period of time during which time the first chemical product is not formed. In some embodiments, third, fourth, fifth, or more chemical products can be formed during subsequent periods of time. For example, in some embodiments, the system can be operated such that the first chemical product is formed over a first period of time (during which time second and third chemical products are not formed), a second chemical product is formed over a second period of time (during which time the first and third chemical products are not formed), and a third chemical product is formed over a third period of time (during which time the first and second chemical products are not formed).

In some embodiments, the first chemical product is compositionally distinguishable from the second chemical product (and/or additional chemical products that are formed using the system). That is to say, the second chemical product can have, in some embodiments, a different chemical formula than the first chemical product. In some embodiments, the compositionally distinguishable first chemical product and second chemical product can be formed using an identical set of modules fluidically connected in series. In certain embodiments, the system is configured to produce at least 1, at least 2 at least 3, at least 4, or at least 5 compositionally distinguishable chemical products.

In some embodiments, the system can be configured to form two or more (e.g., at least two, at least three, at least four, at least five, etc.) compositionally distinguishable products without fluidically connecting unit operations to or disconnecting unit operations from the system between the formation steps. For example, as described above, some embodiments comprise transporting a first fluid through first and second (and/or more) modules to form a first chemical product, and transporting a second fluid through the first and second (and/or more) modules to form a second chemical product. In some such embodiments, no additional unit operations are newly fluidically connected to the first and second modules between the steps of transporting the first fluid and transporting the second fluid. In certain such embodiments, no unit operations are fluidically disconnected from the first and second modules between the steps of transporting the first fluid and transporting the second fluid. That is to say, in some cases, the system is configured such that a first chemical product and a second chemical product can be produced without adding one or more unit operations to and without removing one or more unit operations from the modules in the system.

As one non-limiting example, Examples 2-5 describe the production of diphenhydramine hydrochloride, lidocaine, diazepam, and fluoxetine over separate periods of time between which no unit operations are fluidically disconnected from the synthesis system and no new unit operations are newly fluidically connected to the synthesis system.

Those of ordinary skill in the art would understand that newly fluidically connecting a module and/or unit operation to an existing module and/or unit operation within a system involves establishing a new physical fluidic connection (e.g., using a tube, pipe, or other conduit) between the newly-connected module/unit operation and an existing module/unit operation within the system. In contrast, newly fluidically connecting a module and/or unit operation to an existing system does not simply involve switching the position of a fluidic valve such that fluid is re-routed through an already-connected unit operation/module. Similarly, one of ordinary skill in the art would understand that fluidically disconnecting a unit operation and/or a module from an existing system involves breaking a physical fluidic connection (e.g., by removing a tube, pipe, or other conduit) between the unit operation and/or module and the existing system. In contrast, switching the position of a fluidic valve such that fluid is re-routed away from a unit operation or a module does not constitute fluidically disconnecting that unit operation or module. Accordingly, in some embodiments, a fluid is transported to one or more unit operations in the system, without connecting or disconnecting unit operations within the system, by selecting an appropriate conduit fluidically connected to a manifold and fluidically connected to one or more unit operations within the module, and routing the fluid to be transported through the desired unit operation.

The ability to produce multiple chemical products without the need to remove existing fluidic connections and without the need to establish new fluidic connections can provide a number of advantages, according to certain embodiments. For example, in some instances, first and second chemical products (and, in some cases, additional chemical products) can be produced in a continuous manner without replacing unit operations. In some embodiments, the amount of time between the synthesis of a first product and the synthesis of a second product can be reduced.

Chemical reactants and/or chemical products can be transported into and/or out of the modules and/or unit operations in any suitable form. In certain embodiments, one or more of the chemical reactants and/or chemical products transported through the modules and/or unit operations is in the form of one or more solutes. In certain embodiments, the solute (e.g., the chemical reactant and/or the chemical product) may be present at a relatively high concentration. For example, in some embodiments, a chemical reactant and/or a chemical product may be present at a concentration of greater than or equal to about 1 M. In certain embodiments, a chemical reactant and/or a chemical product may be present in an amount close to the saturation limit (e.g., within 90%, within 95%, or within 99% of the saturation limit) of the chemical reactant and/or of the chemical product. As will be understood by those skilled in the art, the saturation limit generally refers to the concentration of a solute before the solute begins to precipitate from solution (i.e., form a solid phase of the solute). Several advantages of using fluids comprising a high concentration of solutes, as compared to batch processes where dilute solutes are dissolved and/or suspended in a carrier fluid, include increasing productivity and/or processed materials rates and reducing waste and formation of byproducts (e.g., solid precipitates).

In certain aspects, any of the methods for the production of a chemical product (e.g., an ingestible pharmaceutical composition) described herein can be continuous processes. In some embodiments, the method for the continuous production of the chemical product (e.g., the ingestible pharmaceutical composition) comprises transporting an input fluid comprising a chemical reactant through a reactor. In certain embodiments, a chemical reactant is reacted, within a reactor, to produce the chemical product (e.g., an API) within a reactor output stream. In certain embodiments, the reactor output stream is transported to a separator fluidically connected to the reactor in series. For example, referring to FIG. 3A, a chemical reactant within conduit 110 can be transported to module 102, which can contain a reactor. In some embodiments, the chemical reactant from conduit 110 can be reacted within the reactor of module 102 to produce a chemical product (e.g., an API). Some embodiments comprise separating (e.g., in a separator) at least a portion of the chemical product (e.g., an API) from at least a portion of another component of the reactor output stream (e.g., a solvent, etc.) to produce a separator output stream having a higher concentration of the chemical product than the reactor output stream. For example, referring again to FIG. 3A, at least a portion of the output stream from the reactor within module 102 can be transported to module 104. Module 104 can contain a separator (e.g., as described with respect to FIG. 2A). In some embodiments, at least a portion of the chemical product within stream 114 can be separated from another component of stream 114, using the separator within module 104, to produce an output stream 118, which can contain a higher concentration of the chemical product than reactor output stream 114.

Figure 3A:
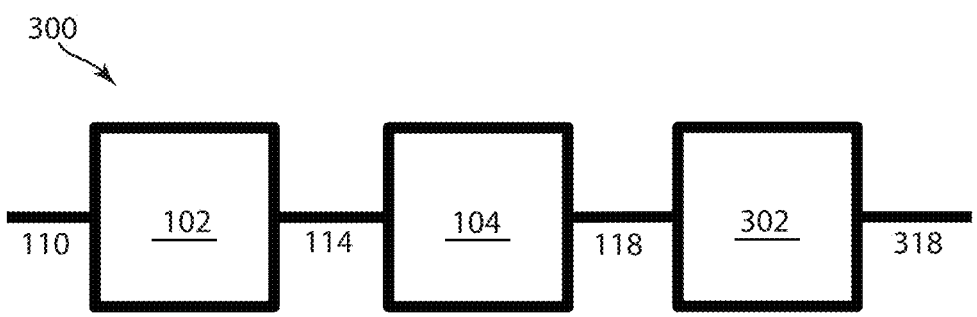
FIG. 3A-B are schematic illustrations of systems for producing chemical products, according to one set of embodiments.

In some embodiments, the separator product stream is transported from the separator to a formulation system, as described below (see, e.g., formulation system 302 in FIGS. 3A-3B). In some embodiments, the separator product stream comprises a chemical product (e.g., an API). In some such embodiments, the chemical product (e.g., API) is a dissolved salt.

One of ordinary skill in the art would understand the difference between a continuous process and a non-continuous process (e.g., a batch process). Continuous processes generally refer to systems in which precursor enters the system, product exits the system, and the transformation the system is designed to achieve all occur during at least a portion of the time during which the transformation occurs. As one example, in a continuous reactor system, reaction precursor enters the reactor and reaction product exits the reactor during at least a portion of the time that the chemical reaction within the reactor is taking place. As another example, in a continuous separator, precursor enters the separator and separated product exits the separator during at least a portion of the time that separation within the separator is taking place. As yet another example, in a continuous crystallizer, at least partially non-crystallized precursor enters the crystallizer and crystallized product exits the crystallizer during at least a portion of the time that the crystallization process within the crystallizer is taking place.

Continuous systems that include two or more unit operations (e.g., reactors, separators, and the like) are generally arranged such that transport between the unit operations within the continuous system occurs during at least a portion of the time during which the unit operations are performing their intended function (e.g., reaction for a reactor, separation for a separator, etc.). Continuous systems that include two or more formulation units (e.g., crystallizers, and the like, as described in more detail below) are generally arranged such that transport between the formulation units within the continuous system occurs during at least a portion of the time during which the formulation units are performing their intended function (e.g., crystallizing for a crystallizer, etc.). Continuous systems that include one or more unit operations and one or more formulation units are generally arranged such that transport between the unit operations and/or the formulation units within the continuous system occurs during at least a portion of the time during which the formulation units are performing their intended function. For example, a continuous reaction and separation system might include, for example, a reactor fluidically connected to a separator in which product from the reactor is transported to the separator during at least a portion of the time during which reaction within the reactor is taking place and separation within the separator is taking place.

In some embodiments, a chemical product is produced continuously from a precursor of the chemical product when precursor of the chemical product is being transported into the continuous system and chemical product is being transported out of the continuous system during at least portions of the times the components of the continuous system are being operated to produce the finished chemical product.

One of ordinary skill in the art would be capable of generalizing the meaning of a continuous process to any type of unit operation and/or combination of unit operations.

In certain embodiments, each unit operation and/or formulation unit within the continuous process (e.g., reactor, separator, crystallizer, filter, etc.) is operated in a continuous fashion such that the products of each unit operation and/or formulation unit are substantially continuously transported from one unit operation and/or formulation unit to the other until the final chemical product is produced. In certain embodiments, at least some of the target chemical product (e.g., at least about 50 wt %, at least about 75 wt %, at least about 90 wt %, at least about 95 wt %, or substantially all of the target chemical product) produced by each upstream unit operation and/or upstream formulation unit within the continuous process is transported to the corresponding downstream unit operation and/or downstream formulation unit within the continuous process within a period of about 12 hours, about 6 hours, about 1 hour, about 30 minutes, about 10 minutes, about 1 minute, or about 10 seconds after it exits the upstream unit operation and/or upstream formulation unit.

In some embodiments, the chemical product is an active pharmaceutical ingredient (API), as discussed in more detail below.

According to certain embodiments, certain of the systems and methods described herein can be used to produce an ingestible pharmaceutical composition. The ingestible pharmaceutical composition can be produced from an API using a formulator, which can contain one or more formulation units. Referring to FIG. 3A, system 300, in certain embodiments, comprises formulation system 302 fluidically connected to one or more modules (e.g., any of the modules described elsewhere herein) in series. Generally, the formulator is configured to add an ingestible component (e.g., an excipient, a binder, etc.) to a mixture containing an API and/or to change the phase of the API within the mixture containing the API. In some embodiments, the formulator adds an ingestible component (e.g., an excipient). In certain embodiments, the formulator converts an active pharmaceutical ingredient to an ingestible form from a non-ingestible form.

Referring again to FIG. 3A system 300 is an exemplary system comprising module 102, module 104, and formulator 302 fluidically connected in series. As described herein, in some embodiments, module 102 and/or module 104 comprises a unit operation. For example, modules 102 and 104 in FIG. 3A can correspond to modules 102 and 104 in FIGS. 1 and/or 2A. In some embodiments, additional modules may also be present.

The method for the production of an ingestible pharmaceutical composition may comprise, in some cases, transporting an input fluid comprising a chemical reactant through a reactor in module 102 via conduit 110 such that the chemical reactant is reacted, within the reactor, to produce an active pharmaceutical ingredient within a reactor output stream. In certain embodiments, the reactor output stream is transported via conduit 114 to module 104. In some embodiments, module 104 comprises a separator. In certain embodiments, the method comprises transporting the reactor output stream to a separator and separating at least a portion of the active pharmaceutical ingredient within the reactor output stream from at least a portion of another component of the reactor output stream to produce a separator product stream. In certain embodiments, the separator product stream has a higher concentration of the active pharmaceutical ingredient than the reactor output stream. In certain embodiments, the separator product stream is transported via conduit 118 to formulator 302, in which the active pharmaceutical ingredient is converted into the ingestible pharmaceutical composition.

In some embodiments, formulator 302 is configured to convert a chemical product (e.g., an API) to an ingestible pharmaceutical composition. In some embodiments, the ingestible pharmaceutical composition is output from formulation system 302 via conduit 318. Formulator 302 may comprise one or more optional formulation units (e.g., a precipitator, a crystallizer, a dissolution unit, a filter, a mixer, and/or a drying unit). For example, in some cases, the formulator may comprise a precipitator. In some embodiments, the formulator comprises two or more precipitators (e.g., a first precipitator and a second precipitator). In some embodiments, the formulator comprises a dissolution unit. In certain embodiments, the formulator comprises a filter. In some embodiments, the formulator comprises a drying unit. In certain embodiments, the formulator comprises a mixer which can be used, for example, to mix the API with a pharmaceutically acceptable excipient. Other formulation units are also possible, as described below.

Figure 3B:
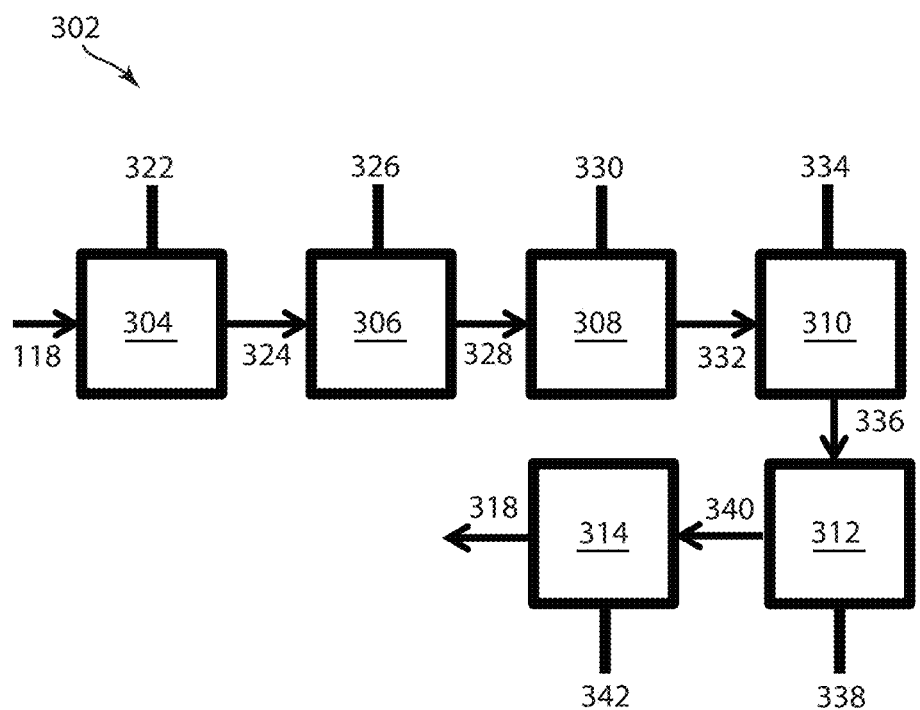

FIG. 3B is a schematic illustration of an exemplary formulator 302, according to certain embodiments. In some embodiments, the formulator comprises a precipitator configured to receive a fluid from a module fluidically connected in series to the precipitator. For example, referring to FIG. 3B, formulator 302 may comprise optional precipitator 304. Precipitator may be fluidically connected to one or more modules, for example, positioned upstream of the precipitator. For example, as illustrated in FIG. 3B, optional precipitator 304 may be configured to receive an input liquid via conduit 320. The input from conduit 320 may originate, for example, from one or more upstream modules. For example, optional precipitator 304 can be located downstream of one or more modules, such as modules 102 and/or 104 illustrated in FIG. 2A.

In some embodiments, precipitator 304 may be configured to receive a second fluid via conduit 322. In certain embodiments, converting the active pharmaceutical ingredient into the ingestible pharmaceutical composition comprises precipitating (e.g., in a precipitator) the active pharmaceutical ingredient from a solution comprising the active pharmaceutical ingredient and a pharmaceutically acceptable carrier.

The precipitator can be configured to facilitate the precipitation of a solid phase from a liquid phase. In certain embodiments, the precipitator can be configured to facilitate the precipitation of a chemical product from a liquid stream containing the chemical product. For example, referring to FIG. 3B, precipitator 304 can receive a liquid input stream containing a chemical product (e.g., a chemical product formed within a module, such as module 102 and/or 104, located upstream of the precipitator). Precipitator 304 can be operated such that the chemical product is precipitated within the precipitator to form a solid chemical product.

In certain embodiments, precipitation comprises formation of the solid via nucleation. Nucleation is a term understood by one of ordinary skill in the art, and is generally used to refer to the beginning of the formation of a solid (e.g., an amorphous solid, a crystalline solid, or a semi-crystalline solid). Nucleation may involve combination of material (e.g., a dissolved precursor) at the molecular scale to form a very small crystal, for example. It should be understood that crystals may exist in many forms, including many polymorphs, solvates and hydrates, for a given crystal material.

In certain embodiments, the precipitator is a crystallizer (e.g., the precipitated solid is a crystalline solid). In certain such embodiments, converting the active pharmaceutical ingredient into the ingestible pharmaceutical composition comprises crystallizing (e.g., in a crystallizer) the active pharmaceutical ingredient from a solution comprising the active pharmaceutical ingredient and a pharmaceutically acceptable carrier. For example, referring again to FIG. 3B, optional precipitator 304 may comprise a crystallizer. Any one of a number of types of crystallizers can be used. For example, in some embodiments, the crystallizer comprises a cooling crystallizer. As will be understood by those skilled in the art, a cooling crystallizer generally operates by decreasing the temperature of a fluid such that solid crystals precipitating upon the cooling of the fluid. In some cases, the cooling crystallizer comprises a mixer. In some embodiments, the crystallizer comprises an anti-solvent crystallization (e.g., an inlet conduit configured to be connected to an anti-solvent agent). As will be understood by those skilled in the art, anti-solvent crystallization generally refers to the use of one or more solvents which reduce the solubility of a solute in the fluid. Combinations of the above crystallizers (e.g., anti-solvent cooling crystallizers) are also possible. Other crystallization methods may also be used and will be known in the art. Non-limiting examples of additional crystallization methods and/or crystallizers include reactive crystallization (e.g., wherein the reaction between two or more components of a fluid result in the formation of a solid crystal) melt crystallization (e.g., wherein the fluid comprises two or more solutes which undergoes crystallization at the same or at different temperatures), evaporation crystallization (e.g., wherein by varying temperature to increase the concentration of a solute in a fluid a solid crystal may form), and the like. In some embodiments, the crystallizer comprises a polytetrafluoroethylene (PTFE) crystallizer. In certain embodiments, the crystallizer comprises a stainless steel crystallizer. Other materials are also possible. Those skilled in the art would be able to select an appropriate material for use as a crystallizer (e.g., a material chemically compatible with one or more solvents and/or solutions contained within the crystallizer).

In some embodiments, the precipitator comprises a vessel such as a tank. In certain embodiments, the vessel of the precipitator has an internal volume of between about 100 mL and about 1 L. In some embodiments, the vessel of the precipitator has an internal volume of at least about 100 mL, of at least about 250 mL, of at least about 350 mL, of at least about 500 mL, or at least about 750 mL. In certain embodiments, the precipitator has an internal volume of less than about 1 L, less than about 750 mL, less than about 500 mL, less than about 350 mL, or less than about 250 mL.

In certain embodiments, the precipitation unit comprises a mixer. Any suitable type of mixer can be used. For example, in some embodiments, the precipitator comprises a impeller which can be used to stir the fluid in the precipitator (e.g., to promote nucleation of a solute). The impeller may rotate at any suitable speed. For example, in some cases, the rotational speed of the propeller impeller may be at least about 50 rpm, at least about 120 rpm, at least about 200 rpm, at least about 320, or at least about 500 rpm.

The precipitator may be configured to operate, in some cases, at a particular temperature. For example, the temperature of a fluid in the precipitator may range between about 0° C. and about 100° C. In some embodiments, the temperature of a fluid in the precipitator may be at least about 0° C., at least about 3° C., at least about 5° C., at least about 10° C., at least about 25° C., or at least about 50° C. In certain embodiments, the temperature of a fluid in the precipitator may be less than about 100° C., less than about 50° C., less than about 25° C., less than about 10° C., less than about 5° C., or less than about 3° C. In some embodiments, the temperature with the precipitator and/or crystallizer is changed during operation. For example, the temperature may change (e.g., increase or decrease) at a rate of greater than or equal to about 0.1° C./min.

In some embodiments, a fluid may be added to the precipitator at a particular flow rate. In certain embodiments, a fluid is added to the precipitator at a flow rate ranging between about 0.1 mL/min and about 5 mL/min. In some cases, for example, the fluid added to the precipitator may have a flow rate of at least about 0.1 mL/min, at least about 0.3 mL/min, at least about 0.5 mL/min, or at least about 2 mL/min. In certain embodiments, the fluid added to the precipitator may have a flow rate of less than or equal to about 5 mL/min, less than or equal to about 2 mL/min, less than or equal to about 0.5 mL/min, less than or equal to about 0.3 mL/min.

In certain embodiments, a fluid may remain in the precipitator for a given amount of time (e.g., a batch time). In some cases, the fluid may remain in the precipitator for at least about 1 hour, at least about 2 hours, at least about 4 hours, at least about 8 hours, or at least about 24 hours. In some embodiments, the fluid may remain in the precipitator for less than or equal to about 24 hours, less than or equal to about 8 hours, less than or equal to about 4 hours, or less than or equal to about 2 hours.

A variety of solvents can be added to the precipitator (e.g., to control the relative saturation of a solute within the precipitator). Exemplary solvents include, but are not limited to methanol, ethanol, ethyl acetate, butyl acetate, isopropyl acetate, propyl acetate, tert-butyl acetate, sec-butyl acetate, acetone, isopropanol, and/or combinations of these. The anti-solvent can include heptane, isopropyl ether, hexyl acetate, isopentyl acetate, pentyl acetate, toluene, 4-methyl-2-pentanone, isopropanol, and/or combinations of these.

In certain embodiments, the formulator comprises a filter. For example, referring to FIG. 3B, formulator 302 comprises optional filter 306. Optional filter 306 may be configured to receive an input liquid via conduit 324. The input from conduit 324 may originate, for example, from optional precipitator 304 and/or one or more upstream modules. For example, optional filter 306 can be located downstream of optional precipitator 304. In some embodiments, optional filter 306 can be located downstream of one or more modules, such as modules 102 and/or 104 illustrated in FIG. 2A.

In some embodiments, filter 306 may be configured to receive a second fluid via conduit 326. In certain embodiments, converting the active pharmaceutical ingredient into the ingestible pharmaceutical composition comprises filtering (e.g., in a filter) a solution comprising the active pharmaceutical ingredient.

The filter can be configured to retain one or more components contained within an input stream as the input stream is transported through the filter. In some embodiments, the filter may perform size-based filtration. For example, the filter may include a porous medium that is configured to retain material having a cross-sectional dimension that exceeds a certain cutoff size, while allowing liquids and smaller solids to pass through. In certain embodiments, the filter may perform filtration based on chemical interactions between the retained component and the filter. For example, the stream input to the filter may contain one or more entities that chemically interact with a medium within the filter (and, thus, be retained by the filter), while the remaining components of the input may not chemically interact with the medium (and, thus, may be passed through the filter).

In certain embodiments, the filter comprises a membrane. Non-limiting examples of filter membranes include Hastelloy filtration membranes, polyvinylidene fluoride membranes, polytetrahydrofloride membranes, or others could be used. In certain embodiments, the average pore size within the membrane modules is between about 0.1 micrometers and about 2 micrometers. Those skilled in the art would be able to select an appropriate filter suitable for use in the filter.

In certain embodiments, the filter comprises a dryer. For example, the filter may comprise a PTFE-dryer. In some embodiments, the filter comprises a high density polyethylene (HDPE) dryer. Other dryers are also possible and will be known to those skilled in the art.

In some embodiments the filter may be configured to operate at a particular temperature (e.g., to evaporate off a solvent). For example, the filter may operate at a temperature ranging between about 40° C. and about 80° C. In some embodiments, the filter may operate at a temperature of at least about 40° C., at least about 50° C., at least about 60° C., or at least about 70° C.

In certain embodiments, the filter may operate under vacuum pressure (e.g., a pressure less than atmospheric pressure). In some embodiments, the vacuum pressure can be maintained at a level suitable to produce effective filtering. If the vacuum pressure is too low, mother liquor and/or the wash material will not be sufficiently removed, and if the vacuum pressure is too high, the wet cake will be too dry to transfer to subsequent formulation units.

In some embodiments, a chemical product (e.g., a crystal) may be present in the filter for a certain amount of time. In certain embodiments, the chemical product may be present in the filter for at least about 10 minutes, at least about 1 hour, at least about 2 hours, or at least about 4 hours.

In some embodiments, the filter described herein may be configured to allow for extremely fast filtration procedures and multiple washing and dilution steps for a precise control of the purity of the pharmaceutically active ingredient and solid loading of the slurries, which can be important in moving material forward within a continuous integrated process.

In some embodiments, the system comprises an optional second precipitator. The optional second precipitator can be configured to receive a fluid from a module and/or another formulation unit fluidically connected in series to the second precipitator. For example, referring to FIG. 3B, formulator 302 may comprise optional second precipitator 308. Optional precipitator 304 may be fluidically connected to one or more additional components, such as one or more upstream modules and/or one or more additional formulation units. For example, referring to FIG. 3B, optional second precipitator 308 may be configured to receive an input liquid via conduit 330. The input from conduit 328 may originate, for example, from one or more upstream modules. In some embodiments, the second precipitator may be a crystallizer. For example, the second precipitator may be any of the crystallizers described above.

In some embodiments, optional second precipitator 308 may be configured to receive a second fluid via conduit 330. In certain embodiments, converting the active pharmaceutical ingredient into the ingestible pharmaceutical composition comprises precipitating (e.g., in the second precipitator) the active pharmaceutical ingredient from a solution comprising the active pharmaceutical ingredient and a pharmaceutically acceptable carrier.

In certain embodiments, the formulator comprises an optional second filter. For example, referring to FIG. 3B, system 302 comprises optional second filter 310. Optional second filter 310 may be configured to receive an input liquid via conduit 332. The input from conduit 332 may originate, for example, from optional precipitator 304 and/or one or more upstream modules. For example, optional second filter 310 can be located downstream of optional precipitator 304. In some embodiments, optional second filter 310 can be located downstream of one or more modules, such as modules 102 and/or 104 illustrated in FIG. 2A.

In some embodiments, optional second filter 310 may be configured to receive a second fluid via conduit 334. In certain embodiments, converting the active pharmaceutical ingredient into the ingestible pharmaceutical composition comprises filtering (e.g., in a second filter) a solution comprising the active pharmaceutical ingredient.

In some embodiments, the formulator comprises a dissolution unit. For example, referring to FIG. 3B, system 302 comprises optional dissolution unit 312. Optional dissolution unit 312 may be configured to receive an input liquid via conduit 336. The input from conduit 336 may originate, for example, from optional precipitator 304, optional filter 306, optional second precipitator 308, optional second filter 310, and/or one or more upstream modules. For example, optional dissolution unit 312 can be located downstream of optional second filter 310. In some embodiments, optional dissolution unit 312 can be located downstream of one or more modules, such as modules 102 and/or 104 illustrated in FIG. 2A.

The dissolution unit may be fluidically connected, in some cases, to the filter in series. In some embodiments, the dissolution unit is fluidically connected so that it receives at least a portion of the retentate produced by the filter. The dissolution unit can be configured to dissolve a solute fed to the dissolution within a solvent fed to the dissolution unit. In some cases, the solute may be an active pharmaceutical ingredient.

In some embodiments, converting the active pharmaceutical ingredient into the ingestible pharmaceutical composition comprises dissolving (e.g., in a dissolution unit) the active pharmaceutical ingredient in a pharmaceutically acceptable excipient, such as a pharmaceutically acceptable carrier.

The dissolution unit can be used, for example, to dilute the filtered product formed in the filter, for example, to make the filtered product more flowable, and therefore, more suitable for use in a continuous manufacturing process. The dissolution unit can include any suitable unit such as, for example, a tank or other suitable chamber in which product can be diluted (e.g., using solvents, as described herein). Examples of units suitable for use in the dissolution unit, for example, include dilution tanks.

In some embodiments, the formulator comprises one or more additional formulation units. For example, referring to FIG. 3B, formulator 302 comprises additional optional formulation unit 314. Optional formulation unit 314 is, in certain embodiments, configured to receive an input liquid via conduit 340. In some such embodiments, optional formulation unit 314 is configured to output an ingestible pharmaceutical composition via conduit 318.

In some embodiments, a diluted stream output from the dissolution unit can be transported to the additional optional formulation unit (e.g., via conduit 340 in FIG. 3B). The additional optional formulation unit can be used to form an ingestible product from an upstream product containing an active pharmaceutical ingredient. The additional optional formulation unit can include a variety a components to form an ingestible pharmaceutical composition. For example, referring to FIG. 3B, additional optional formulation unit 314 might include an extruder or other powder handling system used to produce tablets, ingestible powders, capsules, injectable solution or suspension, or any other suitable form of ingestible pharmaceutical composition. In certain embodiments, the additional optional formulation unit can include a coater, for example, to produce coated tablets and/or capsules. In some embodiments, the additional optional formulation unit is a mixer, as described above. After processing by the additional optional formulation unit, ingestible pharmaceutical compositions (e.g., tablets, capsules, injectable solutions and/or suspensions, etc.) can be transported from the system. In certain embodiments, additional optional formulation unit 314 may be configured to produce an ingestible pharmaceutical composition and dispense the ingestible pharmaceutical composition via conduit 318.

In some embodiments, the one or more formulation units in the formulator may be configured to receive an additional fluid (e.g., a second fluid). For example, referring to FIG. 3B, in some embodiments, precipitator 304 may be configured to receive a second fluid via conduit 322. In certain embodiments, filter 306, crystallizer 308, filter 310, dissolution unit 312, and/or additional formulation unit 314 may be configured to receive a second fluid via conduits 326, 330, 334, 338, and/or 342, respectively. The second fluid may comprise, in some cases, a solvent, an excipient, and/or a binder, as described herein. In some embodiments, precipitator 304, filter 306, crystallizer 308, filter 310, dissolution unit 312, and/or additional formulation unit 314 are configured to output a non-ingestible component from a pharmaceutical-containing mixture via conduits 326, 330, 334, 338, and/or 342, respectively.

In one specific embodiment, formulator 302 comprises multiple formulation units that are fluidically connected in series. Referring to FIG. 3B, the system may comprise, in some cases, six optional formulation units, fluidically connected in series. In some such embodiments, system 302 comprises, precipitator 304, filter 306, crystallizer 308, filter 310, dissolution unit 312, and additional formulation unit 314 fluidically connected in series. Precipitator 304, filter 306, crystallizer 308, filter 310, dissolution unit 312, and formulator 314 may be optional, according to certain embodiments. In other embodiments, formulator 302 comprises a subset of the one or more formulation units fluidically connected in series (e.g., one optional formulation unit, two optional formulation units, three optional formulation units, four optional formulation units, or five optional formulation units). For example, in certain embodiments, formulator 302 comprises precipitator 304, filter 306, and dissolution unit 312. In some embodiments, formulator 302 comprises crystallizer 308, filter 310, and dissolution unit 312. In some such embodiments, precipitator 304 may be fluidically connected to filter 306 in series, and in some such embodiments, precipitator 304 and filter 306 are bypassed and crystallizer 308, filter 310 and dissolution unit 312 are fluidically connected to one or more modules, such as modules 102 and/or 104 illustrated in FIG. 2A.

In some embodiments, the fluid transported through a module and/or a formulation unit, as described above, comprises a solvent. Non-limiting examples of suitable solvents include water, inorganic salt aqueous solutions (e.g., sodium chloride, potassium chloride, ammonium chloride, and ammonium acetate), isopropanol, ethanol, methanol, hexane, heptane, toluene, ethyl acetate, diethyl ether, tert-butyl methyl ether, dioxane, tetrahydrofuran, chloroform, dichloroethane, dichloromethane, N-methyl-2-pyrrolidone, N,N-dimethylformide, N,N-dimethylacetamide, dimethyl sulfoxide, hydrochloric acid, acetone, sodium hydroxide (aqueous solution), or combinations thereof. Other solvents are also possible. Those skilled in the art would be capable of selecting an appropriate solvent.

In some embodiments, the systems described herein may be contained, and/or the methods described herein may be conducted, within a housing. As will be understood by those skilled in the art, a housing generally refers to a frame that at least partially encloses a piece of equipment. The housing can be any suitable material. Non-limiting examples of housing materials include steel, iron, aluminum, plastic (e.g., polyacrylic, polycarbonate, polyethylene, polystyrene), glass, and/or wood. In some embodiments, the housing is open (i.e., the housing comprises one or more openings on one or more sides of the housing). In certain embodiments, the housing is closed.

In some embodiments, the housing within which synthesis systems described herein are contained occupies a relatively small volume. For example, in some embodiments, the housing within which the synthesis systems described herein are contained, while the system is assembled in a functional form, occupies a volume of less than about 100 ft$^3$ or less than about 50 ft$^3$. In some embodiments, the housing within which the synthesis systems described herein are contained, while the system is assembled in a functional form, occupies a footprint of less than about 10 ft$^2$ or less than about 5 ft$^2$. The use of systems with relatively small volumes and/or relatively small footprints can provide a number of advantages, according to certain embodiments. For example, in some embodiments, the compact nature of the system can make it relatively portable, allowing for the production of pharmaceuticals or other chemical products at multiple locations.

In some embodiments, the housing contains a system assembled in functional form comprising a first module comprising at least two unit operations fluidically connected to each other in parallel, a second module comprising at least two unit operations fluidically connected to each other in parallel, and a formulator, wherein the housing occupies a volume of less than about 100 ft$^3$ or less than about 50 ft$^3$. In some embodiments, the housing contains a system assembled in functional form comprising a first module comprising at least two unit operations fluidically connected to each other in parallel, a second module comprising at least two unit operations fluidically connected to each other in parallel, and a formulator, wherein the housing occupies a footprint of less than about 10 ft$^2$ or less than about 5 ft$^2$. In some such embodiments, the formulator within the housing comprises at least one dissolution unit, at least one precipitator, at least one filter, and at least one mixer. In some such embodiments, the formulator within the housing comprises at least one dissolution unit, at least two precipitators, at least two filters, and at least one mixer.

As noted above, certain of the systems and methods described herein can be used to synthesis an active pharmaceutical ingredient ("API"). As used herein, the term "active pharmaceutical ingredient" (also referred to as a "drug") refers to an agent that is administered to a subject to treat a disease, disorder, or other clinically recognized condition, or for prophylactic purposes, and has a clinically significant effect on the body of the subject to treat and/or prevent the disease, disorder, or condition. Active pharmaceutical ingredients include, without limitation, agents listed in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange, 8th edition (Sep. 21, 2000); Physician's Desk Reference (Thomson Publishing); and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005. Preferably, though not necessarily, the active pharmaceutical ingredient is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

In certain embodiments, the active pharmaceutical ingredient is a small molecule. Exemplary active pharmaceutical ingredients include, but are not limited to, anti-cancer agents, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, prostaglandins, etc.

As used herein, the term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible.

Non-limiting examples of APIs include diphenhydramine, lidocaine, diazepam, fluoxetine, ibuprofen, doxycycline, and atropine. Those of ordinary skill in the art, given the present disclosure, would be capable of applying the synthesis methods and systems described herein to other pharmaceutical active ingredients.

Also as noted above, certain of the systems and methods described herein can be used to produce ingestible pharmaceutical compositions. Generally, ingestible pharmaceutical compositions refer to those compositions including an active pharmaceutical ingredient and a pharmaceutically acceptable excipient. As used herein, the term "pharmaceutically acceptable excipient" means a non-toxic, inert solid, semi-solid or liquid filler, diluent, encapsulating material or formulation auxiliary of any type. Some non-limiting examples of materials which can serve as pharmaceutically acceptable excipients are sugars such as lactose, glucose, and sucrose; starches such as corn starch and potato starch; cellulose and its derivatives such as sodium carboxymethyl cellulose, methylcellulose, hydroxypropylmethylcellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; water (e.g., pyrogen free water); isotonic saline; citric acid, acetate salts, Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In some embodiments, the ingestible pharmaceutical composition comprises at least about 2.5 mg, at least about 5.0 mg, or at least about 20 mg of an active pharmaceutical ingredient per milliliter of a pharmaceutically acceptable carrier. In some embodiments, the active pharmaceutical ingredient is dissolved in the pharmaceutically acceptable carrier. In certain embodiments, the active pharmaceutical ingredient is suspended in the pharmaceutically acceptable carrier. In certain embodiments, the ingestible pharmaceutical composition is in the form of a tablet, a pill, or a liquid.

In some embodiments, the system is configured to produce at least about 1000 doses of API per day. In certain embodiments, the system is configured to produce at least about 2000 doses per day, at least about 4000 doses per day, at least about 8000 doses per day, at least about 10000 doses per day, or at least about 20000 doses per day. As will be generally understood by one skilled in the art, the term dose generally refers to an amount of an active pharmaceutical ingredient and/or drug product which is administered to an organism (e.g., a person, an animal, a plant, an insect, and/or a bacterium) to stimulate a biological response. In certain embodiments, the system is configured to produce at least about 20 grams/day, at least about 50 grams/day, at least about 100 grams/day, at least about 200 grams per day, or at least about 400 grams per day of a chemical product (e.g., an ingestible pharmaceutical composition).

In certain embodiments, the system is configured to produce a relatively high amount of an active pharmaceutical ingredient in a small footprint. For example, in some cases, the system may be configured to produce at least about 5 grams of an active pharmaceutical ingredient per square foot footprint area per day. In some embodiments, the system is configured to produce at least about 7 g/day/ft$^2$, at least about 10 g/day/ft$^2$, at least about 20 g/day/ft$^2$, at least about 30 g/day/ft$^2$, at least about 50 g/day/ft$^2$, at least about 60 g/day/ft$^2$, at least about 70 g/day/ft$^2$, at least about 90 g/day/ft$^2$, at least about 100 g/day/ft$^2$, at least about 120 g/day/ft$^2$, at least about 150 g/day/ft$^2$, or at least about 200 g/day/ft$^2$ of an active pharmaceutical ingredient per day per footprint area. In certain embodiments, the system is configured to produce at least about 1 gram of an active pharmaceutical ingredient per cubic feet of a housing (e.g., as described above) per day. For example, in some embodiments, the system is configured to produce at least about 2 g/day/ft$^3$, at least about 3 g/day/ft$^3$, at least about 4 g/day/ft$^3$, at least about 5 g/day/ft$^3$, at least about 7 g/day/ft$^3$, at least about 10 g/day/ft$^3$, at least about 15 g/day/ft$^3$, at least about 20 g/day/ft$^3$, or at least about 25 g/day/ft$^3$ of an active pharmaceutical ingredient per volume of a housing per day.

The following examples are intended to illustrate certain embodiments of the present invention, but do not exemplify the full scope of the invention.

Example 1

This example describes a system in which modules containing various unit operations were arranged in series to perform multiple chemical reactions, according to certain embodiments. Examples 2-5 demonstrate the use of the exemplary system illustrated in FIG. 4A to produce diphenhydramine hydrochloride, lidocaine, diazepam, and fluoxetine through the selection of appropriate modules and unit operations and/or bypasses.

Figure 4A:
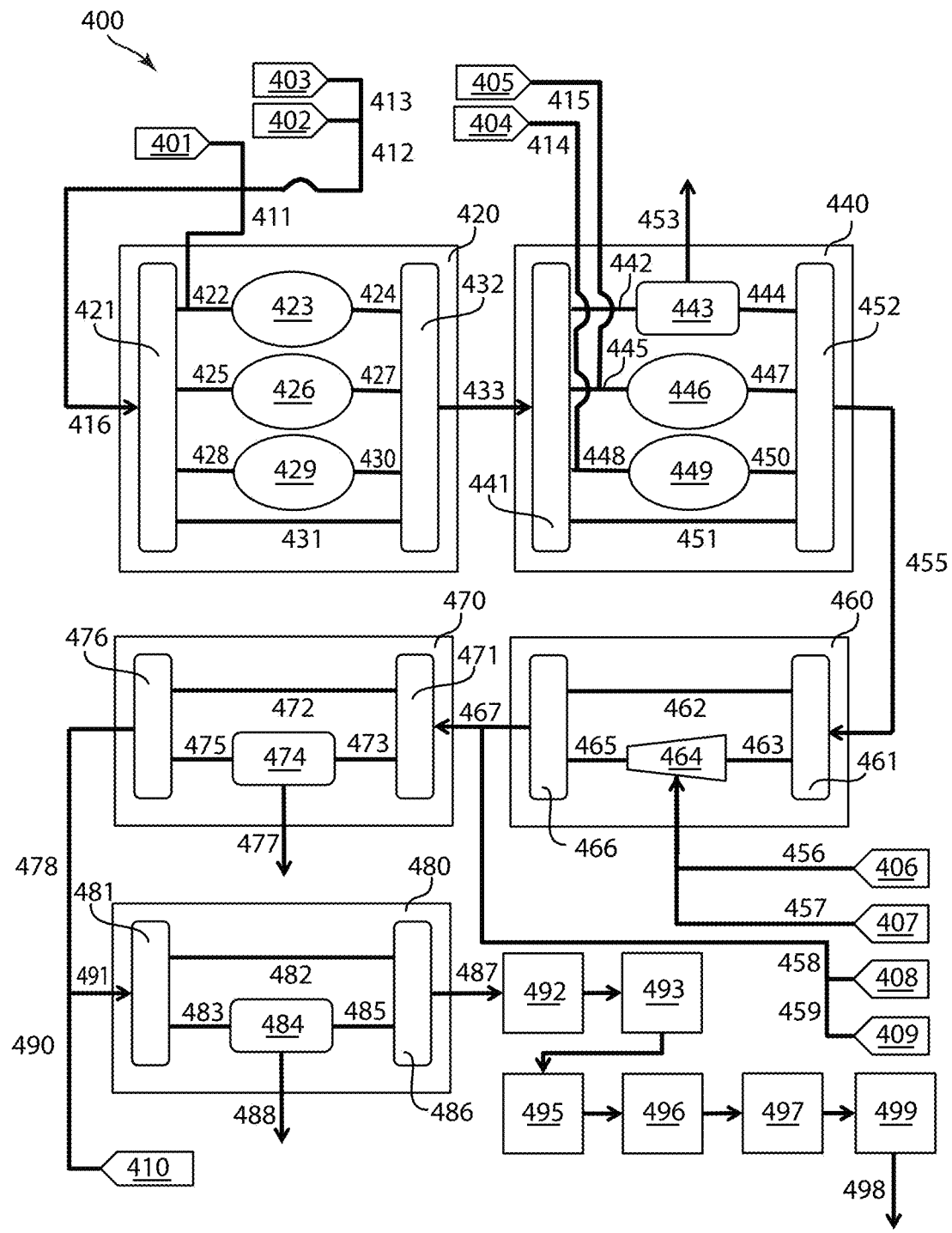
FIG. 4A is a schematic illustration of an exemplary system for producing a chemical product, according to one set of embodiments.

As described in more detail below, to produce a chemical product, a unit operation (e.g., a reactor or a non-reactor unit operation) or bypass was selected in each module to produce the desired sequence of unit operations for a particular chemical synthesis process. Referring to FIG. 4A, System 400 can be operated such that one can switch between one chemical synthesis process (e.g., a process to manufacture diphenhydramine hydrochloride) and another chemical synthesis process (e.g., a process to manufacture lidocaine) simply by actuating one or more valves (e.g., in a manifold) to reroute existing fluidic connections, as opposed to disconnecting existing unit operations and/or connecting new unit operations to the chemical synthesis system.

Figure 4B:
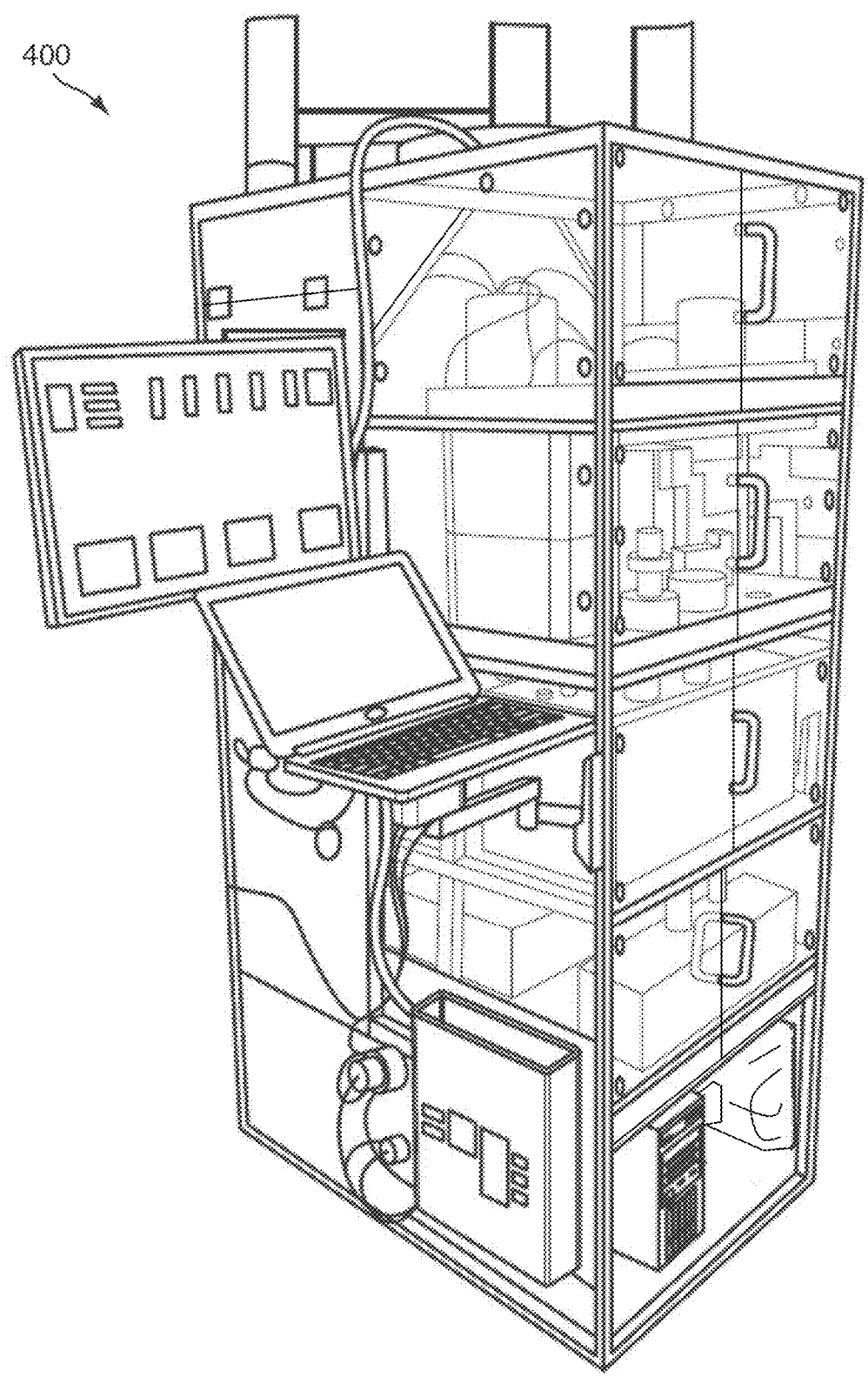
FIG. 4B is a schematic diagram of the exemplary system illustrated in FIG. 4A.

System 400 comprised five modules (420, 440, 460, 470, and 480 in FIG. 4A) fluidically connected in series. System 400 also comprised 10 reservoirs (401, 402, 403, 404, 405, 406, 407, 408, 409, and 410 in FIG. 4A), which were configured to hold the chemical reagents and solvents used to perform the chemical synthesis processes. System 400 also comprised precipitator 492, filter 493, crystallizer 495, filter 496, dissolution unit 497, and formulator 499 fluidically connected in series. Precipitator 492 was fluidically connected in series to module 480. The system occupied a footprint of 0.315 m$^2$ and a volume of 0.551 m$^3$. FIG. 4B is a schematic diagram of exemplary system 400.

Module 420 was configured to receive a fluid from reservoirs 401, 402, and 403 via conduits 411, 412, and 413, respectively. Conduits 412 and 413 were joined at conduit 416, fluidically connected to manifold 421. Conduit 411 was fluidically connected to conduit 422 to optionally add an additional fluid to the input stream to unit operation 423.

Module 420 comprised 10 mL reactor 423, 5 mL reactor 426, 30 mL reactor 429, and bypass conduit 431, fluidically connected in parallel by manifold 421 and manifold 432. Manifold 421 was used to select one or more of reactor 423, reactor 426, reactor 429, via conduit 422, conduit 425, and conduit 428, respectively, and/or bypass conduit 431, to perform a desired step of a chemical synthesis process. Conduit 424, conduit 427, and conduit 430 were fluidically connected and configured to output a fluid (e.g. a chemical product) from reactor 423, reactor 426, and reactor 429, respectively, to manifold 432. Module 440 was fluidically connected in series to module 420 via conduit 433, and was configured to receive one or more fluids from module 420, reservoir 404 via conduit 414 and/or from reservoir 405 via conduit 415. Conduit 414 and conduit 415 were fluidically connected to conduit 445 and conduit 448, respectively.

Module 440 comprised liquid-liquid membrane separator 443, 10 mL reactor 446, 30 mL reactor 449, and bypass conduit 451 fluidically connected in parallel by manifold 441 and manifold 452. The liquid-liquid separator comprised wetted parts in chemically resistant polymeric materials (e.g., PFA, ETFE, PTFE) a rigid housing (e.g. stainless steel, aluminum, other suitable materials) and a semi-permeable membrane. The liquid-liquid separator had a footprint of about 0.05 ft$^2$. The semi-permeable membrane was a PTFE membrane with an average pore size of about 0.5 microns. The separator also comprised a self-tuning pressure regulator comprising PFA (approximately 0.002 inches in thickness). The reactors comprised an internal tubular polymeric coil of defined structure and dimensions embedded in a rigid aluminum housing. Manifold 441 was used to select one or more of separator 443, reactor 446, reactor 449, via conduit 442, conduit 445, and conduit 448, respectively, and/or bypass conduit 451, to perform a desired step of a chemical synthesis process. Conduit 444, conduit 447, and conduit 450 were fluidically connected and configured to output a first fluid (e.g., a chemical product) from separator 443, reactor 446, and reactor 449, respectively, to manifold 452. Conduit 453 was fluidically connected to separator 443 and was configured to remove a second fluid from separator 443.

Module 460 was fluidically connected in series to module 440 via conduit 455, and was configured to receive one or more fluids from module 440, reservoir 406 via conduit 456, and/or reservoir 407 via conduit 457.

Module 460 comprised mixer 464 and bypass conduit 462 fluidically connected in parallel by manifold 461 and manifold 466. Manifold 461 was used to select one or more of mixer 464 via conduit 463 and/or bypass conduit 462, to perform a desired step of a chemical synthesis process. Conduit 456 and conduit 457 were fluidically connected to mixer 464. Conduit 465 was fluidically connected and configured to output a fluid (e.g., a chemical product) from mixer 464 via conduit 465 to manifold 466.

Module 470 was fluidically connected in series to module 460 via conduit 467, and was configured to receive one or more fluids from module 460, reservoir 408 via conduit 458, and/or reservoir 409 via conduit 459. Conduit 458 and conduit 459 were fluidically connected to conduit 467.

Module 470 comprised separator 474 and bypass conduit 472 fluidically connected in parallel by manifold 471 and manifold 476. Manifold 471 was used to select one or more of separator 474 via conduit 473 and/or bypass conduit 472, to perform a desired step of a chemical synthesis process. Conduit 475 was fluidically connected and configured to output a first fluid (e.g., a chemical product) from separator 474 via conduit 475 to manifold 476. Conduit 477 was fluidically connected to separator 474 and was configured to remove a second fluid from separator 474.

Module 480 was fluidically connected in series to module 470 via conduit 491 and was configured to receive one or more fluids from module 470 and/or reservoir 410 via conduit 490. Conduit 491 was fluidically connected to conduit 478 which was fluidically connected to manifold 476, and to conduit 490.

Module 480 comprised separator 484 and bypass conduit 482 fluidically connected in parallel by manifold 481 and manifold 486. Manifold 481 was used to select one or more of separator 484 via conduit 483 and/or bypass conduit 482, to perform a desired step of a chemical synthesis process. Conduit 485 was fluidically connected and configured to output a first fluid (e.g., a chemical product) from separator 484 via conduit 485 to manifold 486. Conduit 488 was fluidically connected to separator 484 and was configured to remove a second fluid from separator 484. Conduit 487 was fluidically connected to manifold 486. Precipitator 492 was fluidically connected in series to module 480 via conduit 487. Precipitator 492 was a HDPE precipitator with a maximum volume of 400 mL.

The fluid was transported from precipitator 492 to filter 493, to crystallizer 495, to filter 496, to dissolution unit 497, and to formulation unit 499 fluidically connected in series. The final chemical product (e.g., an ingestible pharmaceutical composition) was output from conduit 498.

As described in more detail below, appropriate reservoirs and unit operations were selected in the system to produce one or more chemical products. The same system was used for each chemical synthesis, as described below, without fluidically connecting and/or fluidically disconnecting a conduit, a module, a unit operation, or a reservoir.

For illustration purposes, only the modules used in the formation of lidocaine, diazepam, and diphenhydramine chloride are shown in FIG. 4A. It should be noted that module 420, module 440, module 460, module 470, and module 480, as well as precipitator 492, filter 493, crystallizer 495, filter 496, dissolution unit 497, and formulation unit 499 have been simplified for illustration purposes and may comprise one or more additional unit operations (e.g., reactors and/or non-reactor unit operations), one or more additional conduits, and/or one or more additional manifolds, not shown. In some embodiments, conduit 487 was fluidically connected to one or more additional modules and/or a formulator. In system 400, conduit 487 was fluidically connected to precipitator 492. Those skilled in the art would readily appreciate that the synthesis of one or more additional chemical products (e.g., APIs) could also be performed with this system with or without the one or more additional components not illustrated here.

Referring to FIG. 4A, Table 1 summarizes the unit operations selected in each module for the synthesis of diphenhydramine hydrochloride, lidocaine, and diazepam. Referring to FIG. 4A, Table 2 summarizes the contents of each reservoir for the synthesis of diphenhydramine hydrochloride, lidocaine, and diazepam.

TABLE 1

| Module | Diphenhydramine Hydrochloride | Lidocaine | Diazepam |
|---|---|---|---|
| 420 | 10 mL reactor 423 (at 180° C.) | 10 mL reactor 423 (at 120° C.) | 10 mL reactor 423 (at 90° C). |

TABLE 1-continued

| Module | Diphenhydramine Hydrochloride | Lidocaine | Diazepam |
|---|---|---|---|
| 440 | Bypass conduit 451 | 30 mL reactor 449 (at 130° C.) | 10 mL reactor 446 (at 130° C.) |
| 460 | Mixer 464 | Bypass conduit 462 | Bypass conduit 462 |
| 470 | Separator 474 | Separator 474 | Separator 474 |
| 480 | Bypass conduit 482 | Bypass conduit 482 | Separator 484 |

TABLE 2

| Reservoir | Diphenhydramine Hydrochloride | Lidocaine | Diazepam |
|---|---|---|---|
| 401 | Dimethylamino-ethanol | 2,6-Xylidine (1.43M in NMP) | 5-Chloro-2-(methyl-amino)benzophenone (1M in NMP) |
| 402 | | N-Methyl-2-pyrrolidinone (NMP) | N-Methyl-2-pyrrolidinone (NMP) |
| 403 | Chlorodiphenyl-methane | Chloroacetyl chloride | Bromoacetyl chloride |
| 404 | | Et$_2$NH (1.5M in MeOH) KOH (0.5M in H$_2$O) | |
| 405 | | | Ammonia solution (3.5M in MeOH:H$_2$O, 9:1 mixture) |
| 406 | NaOH aqueous solution (3M) | | |
| 407 | Hexane | | |
| 408 | | Hexane | Ethyl acetate |
| 409 | | NaCl/NH$_4$Cl aqueous solution (20 wt % each) | 20% NaCl aqueous solution |
| 410 | | | HCl aqueous solution (4M) |

Example 2

Figure 5:
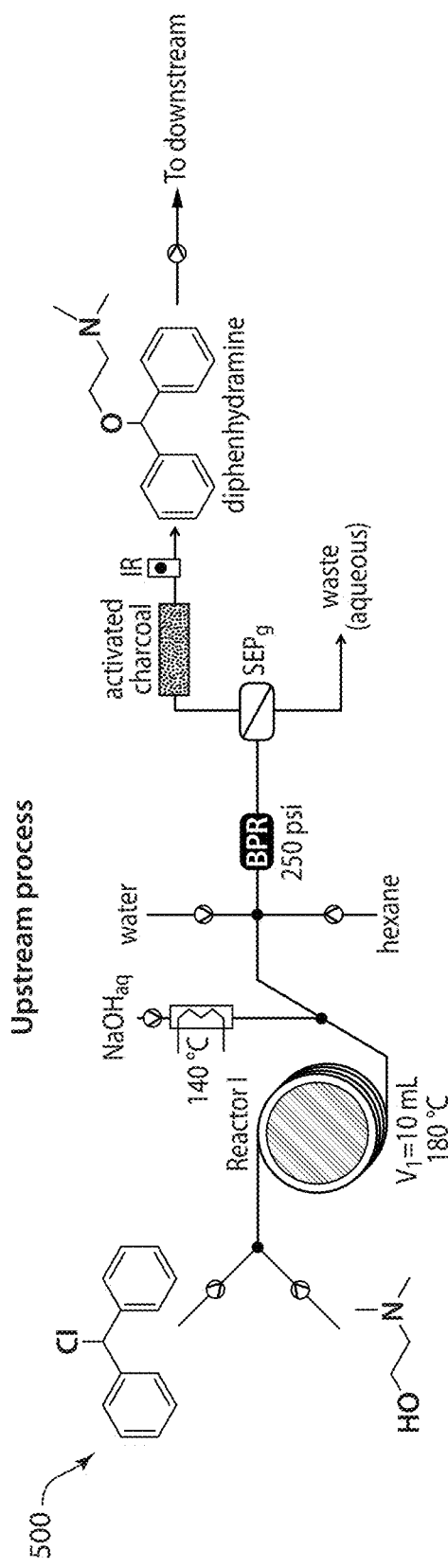
FIG. 5 is, according to some embodiments, a schematic illustration of an exemplary system for producing a chemical product.

This example describes the continuous synthesis and formulation of diphenhydramine hydrochloride using system 400, illustrated in FIG. 4A and described in Example 1. Here, module 420 was selected to use a 10 mL reactor, module 440 was selected to use bypass conduit 451, module 460 was selected to use mixer 464, module 470 was selected to use separator 474, and module 480 was selected to use bypass conduit 482, as outlined in Table 1 and described in more detail, below. The synthesis of diphenhydramine hydrochloride is further illustrated in FIG. 5. It is important to note that no modules, unit operations, and/or conduits were fluidically connected and/or disconnected to the system between the synthesis of diphenhydramine hydrochloride and lidocaine (Example 3), diazepam (Example 4), or fluoxetine (Example 5). That is to say, no new modules, unit operations, or conduits were added to the system and no modules, unit operations, or conduits were removed from the system. Some modules, unit operations, and/or conduits utilized in this example are not illustrated in FIG. 4A for simplification purposes, but are described herein.

Referring again to FIG. 4A, 10 mL reactor 423 was selected to react chlorodiphenylmethane with 2-dimethyl-aminoethanol at 180° C. under a pressure of 250 psi. It should be noted that the reaction was complete within 15 minutes, as compared to a batch process (e.g., 125° C. in benzene for a similar substrate) in which the reaction was completed in greater than five hours. An excess of 2-dimethylamino-ethanol was used to carry the quaternary ammonium salt through reactor 423. 3 M of aqueous sodium hydroxide, preheated to 140° C., was injected after reactor 423 via conduit 456 to quench hydrochloric acid. The extraction of crude diphenhydramine was performed after a back pressure regulator (BPR) by concomitant injection of hexane and water, to remove any remaining 2-dimethylaminoethanol. The diphenhydramine was then passed through a short packed-bed column to improve extraction efficiency (see also FIG. 5) fluidically connected to conduit 467, and the organic phase was separated from the aqueous waste via the selection of a gravity-operated liquid-liquid separator 474. Crude diphenhydramine (82% yield) in hexane was then conveyed, after filtration through activated charcoal, to precipitator 492 for further processing and formulation.

It should be noted that the combination of an excess of 2-dimethylaminoethanol and high temperatures (i.e. temperatures greater than the melting point of the quaternary ammonium intermediate) allowed to keep the processed material flowing in the tubular reactor.

The first step in the downstream process was the precipitation of the crude diphenhydramine (e.g., a crude freebase solution) with hydrochloric acid to form a salt. Approximately, 300 mL of the crude freebase solution was pumped into precipitator 492 and cooled to 10° C. Hydrochloric acid solution in diethyl ether (0.5M) was then added at a rate of 0.5 mL/min while stirring at 200 rpm until a 1:1 molar ratio was obtained. After the addition of the acid was complete, the slurry was stirred for one hour. The precipitated salt was filtered through filter 493, which comprised a HDPE-based dryer with a Hastelloy filtration membrane. The filtered material was washed with 100 mL of cold hexane and then dried in the same unit under vacuum at room temperature for one hour. The dried crude salt was then dissolved in isopropanol at 60° C. so that the concentration was 196.5 mg/mL. The counter-current flow of pre-heated isopropanol at high pressures permitted the transport of large quantities of diphenhydramine salt that would otherwise have not been easily performed. The solution was then crystallized in crystallizer 495 comprising a HDPE crystallizer equipped with a propeller type impeller rotating at 120 rpm. Controlled crystallization of diphenhydramine from isopropanol was achieved because as the solution is hot, isopropanol acts as a solvent, yet on cooling, it becomes an anti-solvent. It would not typically be expected that such a solution could flow and/or that isopropanol would serve as a good anti-solvent. The solution was cooled at 1° C./min to a final temperature of 5° C. The slurry obtained was then filtered and dried in a filter 496 with a drying temperature of 70° C. The purified and dried crystals were then dissolved in water to yield a concentrate in dissolution tank 497. The concentrate was then diluted to a final dosage concentration of 2.5 mg/mL in formulation tank 499. One dose of liquid this liquid formulation is 5.0 ml at a concentration of 2.5 mg/mL. The purity of the final dosage form was measured using HPLC and conformed to the USP standard.

Example 3

This example describes the continuous synthesis and formulation of lidocaine using system 400, illustrated in FIG. 4A and described in Example 1. Here, module 420 was selected to use 10 mL reactor 423, module 440 was selected to use 30 mL reactor 449, module 460 was selected to use bypass conduit 462, module 470 was selected to use separator 474, and module 480 was selected to use bypass conduit 482, as outlined in Table 1 and described in more detail, below. The synthesis of lidocaine is further illustrated in FIG. 6.

Figure 6:
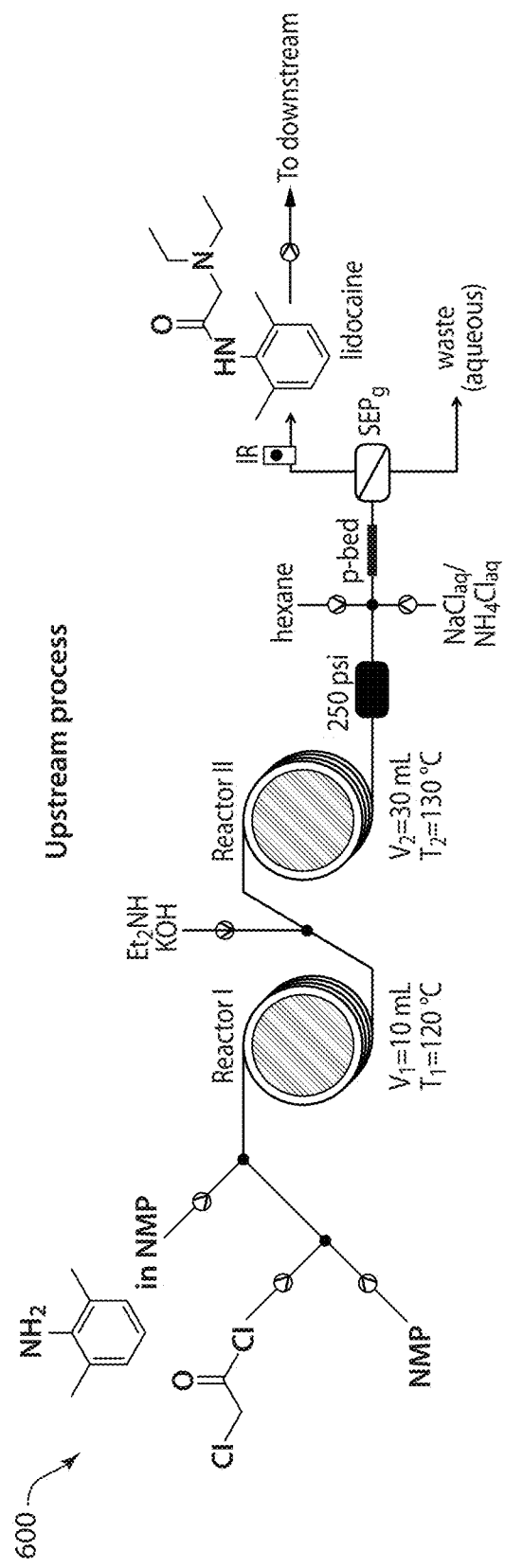
FIG. 6 is a schematic illustration of an exemplary system for producing a chemical product, according to one set of embodiments.

The production of lidocaine consisted of a consecutive 2-step synthesis and a 1-step post-synthetic extraction/separation, all in one continuous flow, as further illustrated in FIG. 6. The first step of synthesis was the direct amidation of 2,6-xylidine with chloroacetyl chloride in N-methyl-2-pyrrolidinone (NMP) in 10 mL reactor 423 at 120° C. The time-dependent decomposition of chloroacetyl chloride in N-methyl-2-pyrrolidinone (NMP) was avoided by mixing streams of both chemicals to form a solution in situ. Upon amidation, a mixture of KOH and diethylamine was introduced to quench HCl generated from prior step and form the tertiary amine moiety in lidocaine. The mixture was added at a temperature of 130° C. (well above the boiling point of diethylamine (55° C.) and several other solvents (methanol and water)) to 30 mL reactor 449. The reaction was complete within 5 minutes (as compared to a batch reaction which required greater than 60 minutes in refluxing toluene or 4-5 hours in refluxing benzene).

The optimal ratio of MeOH and $H_2O$ was critical to dissolve all the intermediates, side-products and final product. The two reactions required 22.4 minutes to reach complete conversion (99%, according to HPLC) from 2,6-xylidine to lidocaine. It should be noted that the amidation between 2,6-xylidine and chloroacetyl chloride through the use of a polar solvent NMP allowed for short reaction times at unusually high concentrations, resulting in high productivity that would not typically be expected within a small footprint.

In order to deliver relatively pure lidocaine solution to the downstream operations and to keep purification as simple as possible, a highly efficient extraction was designed. A mixed sodium and ammonium chloride aqueous solution (2 mL/min) and hexane (3 mL/min) was injected into the outgoing stream (1.65 mL/min) through a cross junction of conduits 459 and 467. The inclusion of a packed-bed column fluidically connected to conduit 467 (see also FIG. 6) with borosilicate beads increased mass transfer, and crude lidocaine in hexane was obtained upon in-line gravity liquid-liquid separation in separator 474. The synthesis/purification sequence was monitored in real-time via in-line infrared spectroscopy. Steady state was reached after 60 minutes and about 90% yield of lidocaine was obtained and delivered to the downstream unit, as a 0.11 M solution in hexane (3 mL/min).

Precipitation was performed in precipitator 492 at 10° C. with a propeller impeller stirred at 320 rpm. Once 250 mL of crude solution has entirely been pumped into the precipitation unit, 82.5 mL of 0.5 M HCl in diethyl ether was added at a flow rate of 0.1 mL/min. The molar ratio of HCl to crude was 1.5:1. Lidocaine hydrochloride was obtained after 8 h holding time with a yield of about 95% and a purity of 93.6%.

The slurry was then drained into filter 493. After the mother liquor (ML) was filtered, the crystals were washed with 250 mL of hexane while filtering the ML. Once the washing liquid (WL) was filtered, the produced filter cake was dried under vacuum in the filter at 50° C. for 60 min.

Recrystallization was then performed in crystallizer 495 using an antisolvent (e.g., hexane) cooling crystallization process (cooling from 50° C. to 5° C.) with a holding time of 2 h at 5° C. A mixture of acetone/isopropanol (96:4) was used as the solvent. Hexane (40 vol %) was added with a flow rate of 2 mL/min at 50° C. while cooling down with 1° C./min. The crystallizer was stirred with a propeller impeller at 200 rpm. The initial concentration was 34.6 mg/mL. After 2 h of holding time at 5° C., a yield of 87.6% with a purity of 97.7% was achieved.

The purified crystals were next drained into filter 496. After the ML was filtered, the crystals were washed with 100 mL of hexane (pumped into the crystallizer) while filtering the ML. Once the WL was filtered, the filter cake was dried under vacuum at 50° C. for 120 min in filter 496. Once the drying was finished, 50 mL of a premixed solution comprising 4% sodium carboxymethyl cellulose in water was added to re-suspend and dissolve the crystals with a stirring rate of 200 rpm in dissolution unit 497. The solution was drained into formulation tank 499.

The concentration was verified employing an ultrasound probe and then was be diluted to a final dosage of 20 mg/mL.

Example 4

This example describes the continuous synthesis and formulation of diazepam using system 400, illustrated in FIG. 4A and described in Example 1. Here, module 420 was selected to use 10 mL reactor 423, module 440 was selected to use 10 mL reactor 446, module 460 was selected to use bypass conduit 462, module 470 was selected to use separator 474, and module 480 was selected to use separator 484, as outlined in Table 1 and described in more detail, below. The synthesis of diazepam is further illustrated in FIG. 7.

Figure 7:
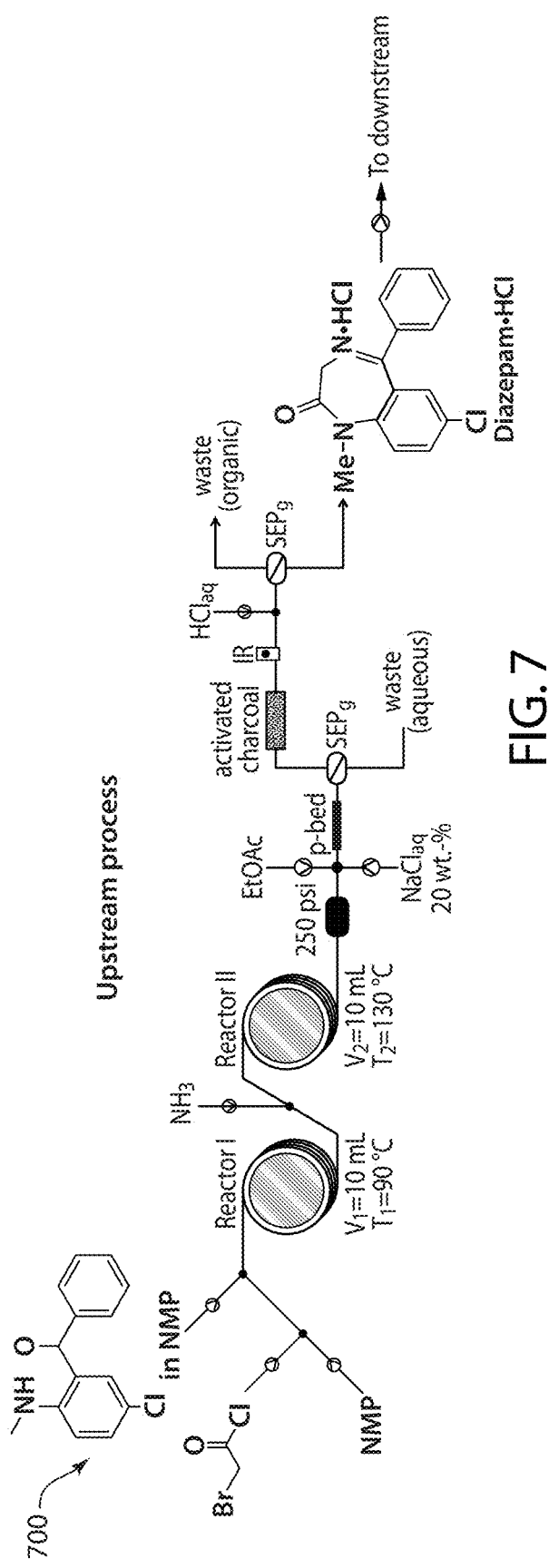
FIG. 7 is a schematic illustration of an exemplary system for producing a chemical product, according to one set of embodiments.

The synthesis for the production of diazepam involved a three-step continuous process, as further illustrated in FIG. 7. 10 mL reactor 423 and 10 mL reactor 446 were selected, operated at 90° C. and 130° C., respectively. Bromoacetyl chloride was utilized instead of chloroacetyl chloride in order to prevent the clogging of reactor 446 and hence ensure a high output in diazepam, enabling highly efficient amination/intramolecular imine formation at low water ratio (MeOH/$H_2O$=9:1) without causing extensive salt formation. Under optimal conditions, conversion of starting materials reached greater than 95%, producing diazepam at 78% yield (HPLC). Analysis of the crude mixture revealed several side products, including starting 5-chloro-2-(methylamino)benzophenone intermediate halides, and their hydrolysis adducts and as well as dimers/trimers.

It should be noted that diazepam is generally poorly soluble in water, and moreover, the synthesis of diazepam in two consecutive steps generates several different salts that are poorly soluble in organic solvents. The use of optimal reagents (e.g., bromoacetyl chloride) and optimal solvent combinations (e.g., water, NMP, and/or MeOH) permitted the production of diazepam in one continuous flow without clogging of the system. Additionally, the reaction was conducted at 130° C. in 10 mL reactor 446, well above the boiling point of ammonia (−33° C.) and several other solvents used in the process (e.g., methanol and water). The reaction was complete within five minutes (as compared to a batch process with required greater than 24 hours in methanol for similar substrates).

The subsequent continuous purification setup was designed to efficiently remove all side products and impurities, some of which having very similar properties (e.g., solubility, pKa, etc.) with diazepam itself. The purification setup combined three consecutive stages consisting of extractions and filtrations. A first continuous extraction of the reaction mixture with aqueous sodium chloride (20 wt.-%) and ethyl acetate separated diazepam from water soluble side-products generated in the process Then, the acetyl acetate extract was passed through a cartridge fluidically connected to conduit 467 and loaded with activated charcoal to remove dark colored by-products (e.g. dimers and trimers). At this point, an in-line silicon infrared (IR) probe was inserted for real-time monitoring. Finally, a continuous extraction with aqueous HCl (4 M) was performed, separating organic impurities (in ethyl acetate) from the conjugated acid of diazepam (in water). The continuous separation was carried out using gravity-based liquid-liquid separators. The process delivered diazepam hydrochloride in water (0.1 M) that was conveyed to the next module for advanced purification.

Precipitation was performed in precipitator 492 at 10° C. with a propeller impeller stirred at 320 rpm. Once 250 mL of crude solution was entirely pumped into the precipitator, 93 mL of 28% aqueous ammonium hydroxide was added with a flow rate of 0.3 mL/min. The overall holding time was 24 h with a yield of about 95% and a purity of 96.7%. The slurry from the precipitator was drained into filter 493. After the mother liquor (ML) was filtered, the crystals were washed with 250 mL of water (pumped into the precipitator) while filtering the ML. Once the washing liquid (WL) was filtered, the resultant filter cake was dried under vacuum at 50° C. for 60 min in filter 493. The recrystallization was conducted in crystallizer 495 using an antisolvent (water) crystallization at 25° C. with a holding time of 2 h and dimethylsiloxane (DMSO) as solvent. Water (70 vol %) was added with a flow rate of 2 mL/min. The crystallizer was stirred with a propeller impeller at 200 rpm. The initial concentration produced was 21.6 mg/mL. After 2 h of holding time at 25° C., diazepam was obtained in 93.6% (104.3% purity). Next, the slurry was drained into filter 496. After the ML was filtered, the crystals were washed with 100 mL of water (pumped into the crystallizer) while filtering the ML. Once the WL was filtered, the resultant filter cake was dried under vacuum at 60° C. for 240 min in filter 496. After drying, 40 mL of ethanol was added to re-suspend and dissolve the crystals with a stirring rate of 200 rpm in dissolution unit 497. When the solution was drained into formulation tank 499, the concentration was measured using ultrasound to be 7.83 mg/mL and then adjusted by the operator to the final dose concentration of 5.263 mg/mL. The operator could also dilute the concentrated diazepam/ethanol solution with water to obtain the final dose concentration of 1 mg/mL (comprising 19 vol % Ethanol).

Example 5

This example describes the continuous synthesis and formulation of fluoxetine using the system described in Example 1. As described below, reactors, unit operations, and bypasses were selected from system 400 (FIG. 8) to perform the appropriate reaction steps.

It is important to note that no modules, unit operations, and/or conduits were fluidically connected and/or disconnected to the system between the synthesis of fluoxetine and diphenhydramine hydrochloride (Example 2), lidocaine (Example 3), or diazepam (Example 4). That is to say, no new modules, unit operations, or conduits were added to the system and no modules, unit operations, or conduits were removed from the system. Some modules, unit operations, and/or conduits utilized in this example are not illustrated in FIG. 4A for simplification purposes, but are described herein. For example, the synthesis and formulation of fluoxetine utilized system 400 as illustrated in FIG. 4A, by selecting four reactors, four separators, a heat exchanger, and a molecular sieve, fluidically connected but not shown in FIG. 4A.

Key challenges overcome included the ability to perform reactions in-line for forward chemical compatibility (pressurized liquid/liquid extractions, 250 psi), efficiency of extractions, precise control of the internal fluid pressure (single chamber multi-inlet pressure regulators to enable liquid/liquid extractions with membrane separators), dealing with solid formation (Aluminates, KOH, KF), presence of water in reaction solvents, retarded rates of reaction (presence of toluene in final step), and obtaining the crude API as a solution directly transferable and usable for downstream processing.

Figure 8:
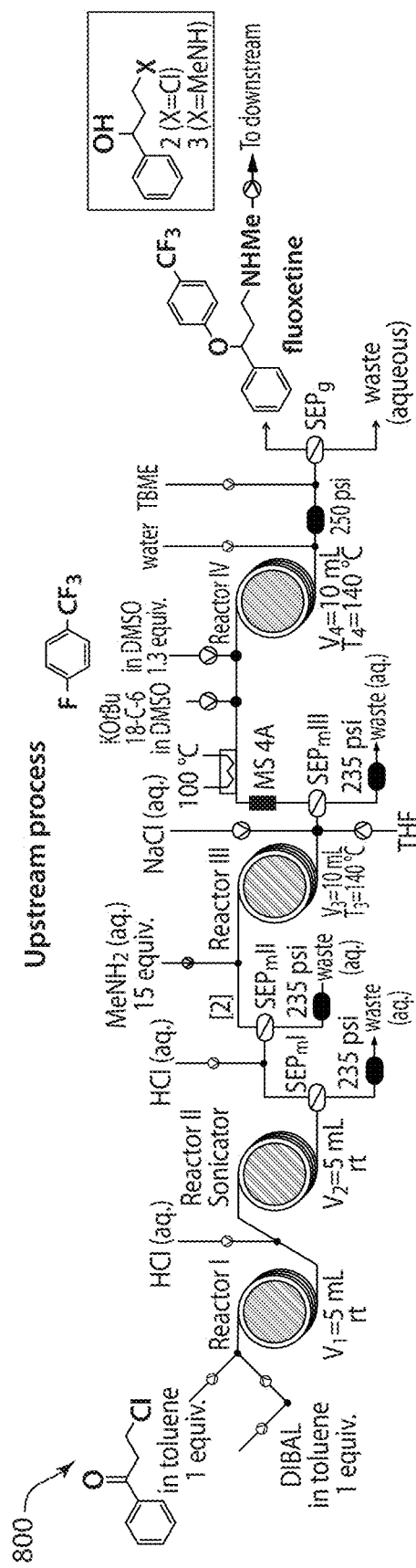
FIG. 8 is, according to some embodiments, a schematic illustration of an exemplary system for producing a chemical product.

The continuous flow synthesis of fluoxetine, as illustrated in more detail in FIG. 8, started with a DIBAL (1 M in toluene) reduction of 3-chloropropiophenone (3 M in toluene) carried out in 5 mL spiral reactor (Reactor I in FIG. 8). 3-chloropropiophenone was close to saturation. The reduction proceeded smoothly at room temperature and reached completion within 10 min at 0.36 mmol/min scale (96% yield).

Aluminum salts were not compatible with the subsequent amination reaction, thus requiring removal; however, their quench (4 M HCl, aq.) generated copious amounts of solids. An ultrasonic transducer enabled fast dissolution of the salts and hence continuous operation. A two-stage in-line extraction and separation sequence was implemented with successive membrane liquid-liquid separators (SEPm I and II, FIG. 8) for removing aqueous waste and gas from DIBAL decomposition. A second stream of aqueous 4 M HCl was injected in the system before SEPm II allowing for complete quench. The intermediate alcohol was obtained in 91% yield post-separation.

The intermediate alcohol (0.75 M in the main toluene stream) was then directed to reactor III (FIG. 8) where it reacted with aqueous methylamine (11.5 M, 15 equivalents). Segmented-flow conditions allowed for fast transfer of methylamine from the aqueous droplets toward toluene and also solvation of ammonium salts. The conversion of the starting alcohol reached 93% after 10 min of residence time in a 10 mL spiral reactor set at 140° C. (89% yield). The reaction temperature of 140° C. is well above the boiling point of methylamine (and close to the critical point of methylamine) and several of the solvents used (e.g., methanol and toluene). The reaction was completed within 10 minutes.

The third separation step was especially challenging due to contrasting needs of the extraction in view of the subsequent $SN_{Ar}$ reaction. Poor solubility of the desired aminoalcohol in toluene and formation of an emulsion at the reactor outlet precluded efficient in-line separation (33% yield after extraction), while the SNAr was particularly dependent on use of water-miscible, polar solvents where hydrophobic solvents highly hampered reactivity. As such, tetrahydrofuran (THF) was used as an extraction solvent. By ionizing the aqueous layer with sodium chloride (20 wt.-%), THF became water-immiscible, efficiently extracting the aminoalcohol (90% after in-line separation), while not posing a hindrance to the aromatic substitution. Other solvents were investigated such as diethyl ether, dimethoxyethane, dimethylsulfoxide (DMSO), dimethylformamide (DMF), and sulfolane which either failed to extract the intermediate aminoalcohol or caused clogging.

Though the extraction was efficient, $H_2O$ solubility in THF was non-negligible, and the coexistence of water and potassium tert-butoxide led to precipitation of KOH and clogging in reactor IV. Selection of a molecular sieve in the seventh module (MS, 4 Å, FIG. 8) circumvented this outcome.

Just upstream of reactor IIV (10 mL, 140° C.), the dried and preheated stream of aminoalcohol came into contact with consecutive streams of potassium tert-butoxide/18-

Crown-6, 0.25 M and 0.05 M in DMSO, respectively, and 4-fluorobenzotrifluoride in DMSO (0.24 M), yielding crude fluoxetine.

Just downstream reactor IV, a stream of water was injected before the BPR to avoid precipitation of potassium fluoride and other salts, and prevent clogging of the BPR. The main effluent was then extracted by a stream of tert-butyl methyl ether (TBME) and the organic phase was separated from the aqueous waste via a final gravity-operated liquid-liquid separator. Crude fluoxetine in TBME was then conveyed with a flow rate of 4.6 mL/min and a concentration of 7.5 mg/mL from the upstream to the downstream unit for further processing and formulation. Precise control of pressure regulation was an important consideration.

Precipitation was performed at 3° C. with a propeller impeller stirred at 320 rpm in precipitator 492. The precipitator was loaded with about 50 mg of fluoxetine HCl seed crystals before the crude solution was pumped. Once 300 mL of crude solution was pumped into the precipitator, 10 mL of 2 M HCl solution in diethyl ether was added at a flow rate of 0.5 mL/min. Then, 60 mL of hexane (antisolvent) was added with a flow rate of 0.5 mL to lower the solubility of fluoxetine hydrochloride in the solution. The resulting slurry was allowed to remain in solution for at least 8 hours. The precipitated salt was then filtered using a specially constructed filter/dryer unit made of HDPE with a Hastelloy filtration membrane and washed with 250 mL of hexane in filter 493. Once the washing liquid (WL) was filtered, the resulting filter cake is dried under vacuum at 50° C. for 60 min in filter 493.

The dried crude salt was then dissolved in acetone at 50° C., and the solution was crystallized in crystallizer 495 in a HDPE crystallizer equipped with a PTFE propeller type impeller rotating at 120 RPM. The recrystallization was performed in a two stage antisolvent (hexane) cooling crystallization process (cooling from 50° C. to 5° C.) with a holding time of 2 h at 5° C. Hexane (37.5%) was added at 50° C. and cooled down at 1° C./min. The concentration in stage one was 26.3 mg/mL and 21.2 mg/mL in stage two. The average yield of both stages was 74% with a purity of 93.0 and 102.0%, respectively.

The resulting slurry was then filtered and dried in filter 496 at 70° C. The purified and dried crystals were then dissolved in water to yield a concentration of 4 mg/mL in dissolution unit 497. With such formulation, 5 mL represents one dose, i.e. 20 mg of fluoxetine hydrochloride. The purity of the final dosage form was measured using HPLC and conformed to the USP standard.

Example 6

Table 3 summarizes the dosage and rate of synthesis of the system used for the synthesis of diphenhydramine, lidocaine, diazepam, and fluoxetine, as described in Examples 2-5.

Typically, a single 1000 gram batch production of lidocaine would require about 500 liters of hexane and at least a 1000 liter batch reactor (e.g., for the liquid-liquid extraction/separation steps). In contrast, the system described herein sustained the separation of 1000 grams of lidocaine with a compact continuous liquid-liquid separator in a complete system occupying a footprint of approximately 0.551 m$^3$ (551 liters).

TABLE 3

|  | diphenhydramine | lidocaine | diazepam | fluoxetine |
|---|---|---|---|---|
| g/day | 439 | 225 | 195 | 22 |
| dosage (mg) | 20 | 100 | 10 | 10 |
| doses/day | 21,950 | 2,250 | 19,500 | 2,200 |
| kg/year | 160 | 82 | 71 | 8 |
| doses/year | 8,011,750 | 821,250 | 7,117,500 | 803,000 |
| g/day/m$^2$ | 1,394 | 714 | 619 | 70 |
| g/day/m$^3$ | 796 | 408 | 354 | 40 |
| doses/day/m$^2$ | 69,683 | 7,143 | 61,905 | 6,984 |
| doses/day/m$^3$ | 39,819 | 4,082 | 35,374 | 3,991 |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for producing chemical products, comprising:
    transporting a first fluid comprising a first chemical reactant through a first module comprising a chemical reactor and at least a second unit operation fluidically connected in parallel, and through a second module connected to the first module in series, the second module comprising at least one separator and at least a fourth unit operation fluidically connected in parallel, such that the first chemical reactant within the first fluid is reacted to form a first chemical product that is transported out of the second module; and
    subsequently, transporting a second fluid comprising a second chemical reactant through the first module and the second module such that the second chemical reactant within the second fluid is reacted to form a second chemical product, without forming the first chemical product, such that the second chemical product is transported out of the second module;
    wherein:
        no additional unit operations are newly fluidically connected to the first and second modules between the steps of transporting the first fluid and transporting the second fluid, and
        no unit operations are fluidically disconnected from the first and second modules between the steps of transporting the first fluid and transporting the second fluid.

2. The method of claim 1, further comprising transporting the first fluid through the at least one separator and separating the first fluid into a first stream containing the first chemical product and a second stream containing a first chemical byproduct.

3. The method of claim 1, wherein the first and/or second chemical products is an active pharmaceutical ingredient (API).

4. The method of claim 3, wherein the API is diphenhydramine, lidocaine, diazepam, or fluoxetine.

5. The method of claim 3, wherein the API is processed downstream into a tablet, a pill, or a liquid.

6. The method of claim 3, wherein the first and/or second chemical product contains at least about 2.5 mg of the API per milliliter suspended in a pharmaceutically acceptable carrier.

7. The method of claim 1, wherein the reactor has a volume of less than or equal to about 1 L.

8. The method of claim 1, wherein the reactor is operated at a pressure of greater than or equal to about 200 psi.

9. The method of claim 1, wherein the reactor is operated at a temperature of greater than or equal to about 60° C.

10. The method of claim 1, further comprising, after transporting the first chemical product out of the second module and before transporting the second chemical product out of the second module, rerouting existing fluidic connections between the first module and the second module via a manifold fluidically connected to the first module and the second module.

11. A method for the continuous production of an ingestible pharmaceutical composition within a reactor system, comprising:
    transporting an input fluid comprising a chemical reactant through a reactor such that the chemical reactant is reacted, within the reactor, to produce an active pharmaceutical ingredient within a reactor output stream;
    transporting the reactor output stream to a separator and separating at least a portion of the active pharmaceutical ingredient from at least a portion of another component of the reactor output stream to produce a separator product stream having a higher concentration of the active pharmaceutical ingredient than the reactor output stream; and
    transporting the separator product stream from the separator to a formulator in which the active pharmaceutical ingredient is converted into the ingestible pharmaceutical composition,
    wherein the amount of the active pharmaceutical ingredient within the ingestible pharmaceutical composition that is output from the formulator is output at a rate of at least about 20 grams/day, and
    wherein the reactor system, including the reactor, the separator, and the formulator, are contained within a housing occupying a volume of less than about 100 ft$^3$ and/or occupying a footprint of less than about 10 ft$^2$.

12. The method of claim 11, wherein the housing occupies a footprint of less than about 10 ft$^2$.

13. The method of claim 11, wherein the housing occupies a volume of less than about 100 ft$^3$.

14. The method of claim 11, wherein the active pharmaceutical ingredient is diphenhydramine, lidocaine, diazepam, or fluoxetine.

15. The method of claim 11, wherein the ingestible pharmaceutical composition is a tablet, a pill, or a liquid.

16. The method of claim 11, wherein the reactor has a volume of less than or equal to about 1 L.

17. The method of claim 11, wherein the reactor is operated at a pressure of greater than or equal to about 200 psi.

18. The method of claim 11, wherein the reactor is operated at a temperature of greater than or equal to about 60° C.

19. The method of claim 11, wherein the formulator comprises a precipitator, a filter, and/or a dissolution tank.

20. The method of claim 11, wherein converting the active pharmaceutical ingredient into the ingestible pharmaceutical composition comprises:
   precipitating the active pharmaceutical ingredient from a solution comprising the active pharmaceutical ingredient and a pharmaceutically acceptable solvent, and/or crystallizing the active pharmaceutical ingredient from a solution comprising the active pharmaceutical ingredient and a pharmaceutically acceptable solvent, and/or diluting the active pharmaceutical ingredient with a pharmaceutically acceptable solvent.

21. The method of claim 11, wherein the reactor output stream and/or separator product stream is transported without a pump.

* * * * *